(12) United States Patent
Yang

(10) Patent No.: US 8,992,949 B1
(45) Date of Patent: Mar. 31, 2015

(54) BIOCOMPATIBLE POLYMERIC COMPOSITIONS HAVING MICROCRYSTALLINE AND AMORPHOUS COMPONENTS AND METHODS FOR THEIR MANUFACTURE

(71) Applicant: Shih-Liang Yang, Laguna Hills, CA (US)

(72) Inventor: Shih-Liang Yang, Laguna Hills, CA (US)

(73) Assignee: Unicare Biomedical, Inc., Laguna Hills, CA (US)

( * ) Notice: Subject to any disclaimer, the term of this patent is extended or adjusted under 35 U.S.C. 154(b) by 0 days.

(21) Appl. No.: 13/667,357

(22) Filed: Nov. 2, 2012

Related U.S. Application Data

(60) Provisional application No. 61/629,362, filed on Nov. 17, 2011.

(51) Int. Cl.
| | | |
|---|---|---|
| *A61K 9/00* | (2006.01) | |
| *A61K 9/10* | (2006.01) | |
| *A61K 47/06* | (2006.01) | |
| *A61K 47/34* | (2006.01) | |
| *A61K 45/00* | (2006.01) | |

(52) U.S. Cl.
CPC ............... *A61K 47/34* (2013.01); *A61K 45/00* (2013.01)
USPC ....................................... 424/400; 514/772.7

(58) Field of Classification Search
USPC ....................................................... 424/400
See application file for complete search history.

(56) References Cited

U.S. PATENT DOCUMENTS

| | | |
|---|---|---|
| 4,191,747 A | 3/1980 | Scheicher |
| 5,073,373 A | 12/1991 | O'Leary et al. |
| 5,290,558 A | 3/1994 | O'Leary et al. |
| 5,356,629 A | 10/1994 | Sander et al. |
| 6,281,195 B1 | 8/2001 | Rueger et al. |
| 7,553,913 B2 | 6/2009 | Wellisz et al. |
| 7,829,616 B2 | 11/2010 | Wellisz et al. |
| 8,124,687 B2 | 2/2012 | Wellisz et al. |
| 2003/0095945 A1 | 5/2003 | Levy et al. |
| 2006/0100370 A1 | 5/2006 | Wellisz et al. |
| 2006/0140904 A1 | 6/2006 | Wellisz et al. |
| 2009/0238758 A1 | 9/2009 | Wellisz et al. |
| 2009/0286886 A1* | 11/2009 | Fisher et al. ............... 514/772.3 |

OTHER PUBLICATIONS

Alli et al., "Synthesis, characterization and surface properties of amphiphilic polystyrene-b-polypropylene glycol block copolymers", 2006, European Polymer Journal, vol. 42, pp. 740-750.*

* cited by examiner

*Primary Examiner* — Michael B Pallay
(74) *Attorney, Agent, or Firm* — Stout, Uxa & Buyan, LLP; Carlos A. Fisher

(57) ABSTRACT

Compositions comprising a polymer-based macroscopically homogeneous polymer alloy comprising a plurality of microcrystalline components dispersed within an amorphous component, which is biocompatible, bioerodable, substantially non-toxic, and excretable, or metabolized when introduced into a mammalian body. In preferred embodiments, malleable molded devices such as implants, films, drug delivery systems and the like, are comprised of the compositions. Methods of making such compositions by controlled cooling of the molten alloy are also described.

35 Claims, 8 Drawing Sheets

Cooling Profiles of PLURONIC® P85 and F88 Blend, and P85 and F88 Alone, Respectively.

Cooling Profiles of 50:50 Ratio of PLURONIC® P123 and F127 Blend, P123 and F127 Alone, Respectively Illustrative Dissolution Pattern of 60:40 of Blend of P123 and F127

Simulated Cooling Profiles - Effect of Molten Temperature on Cooling Rate

BIOCOMPATIBLE POLYMERIC COMPOSITIONS HAVING MICROCRYSTALLINE AND AMORPHOUS COMPONENTS AND METHODS FOR THEIR MANUFACTURE

This patent application is a non-provisional of Provisional Patent Application 61/629,362, filed Nov. 16, 2012, which is hereby expressly incorporated herein by reference in its entirety.

FIELD OF THE INVENTION

The present invention relates to biocompatible compositions and methods of their use and manufacture. The compositions of the present application are suitable, without limitation, for use in the medical, dental, pharmaceutical and veterinary arts. In certain embodiments the invention pertains to compositions for use as a bone-healing component, for example, a bone graft or "wax" capable of being molded or injected for placement at, for example, a surgical site, as well as their manufacture. The bone-healing component aids in stemming the flow of blood and promoting healing at the surgical site. The compositions, in certain embodiments may have inherent biological activity, thereby aiding in the healing process. Additionally, in certain related embodiments the composition may comprise a carrier, such as one or more additional agents having medical, dental, veterinary or biological benefit, such as a drug or other bioactive component. In certain embodiments the bioactive component may comprise bioactive glass or other agents, such as biological response modifiers.

The compositions of the invention comprise biocompatible, and substantially non-toxic compositions capable of being excreted, absorbed and/or metabolized by the patient or subject.

BACKGROUND AND USES OF THE INVENTION

In the medical, dental, pharmaceutical and veterinary arts there is a need for compositions having highly reproducible characteristics selected from one or more of the following: malleability (from a viscous "oily" liquid or gel to a solid "waxy" material), biocompatibility, low toxicity, the ability to be excreted or otherwise eliminated by the patient, easy and inexpensive to manufacture, and being readily altered to a variety of viscosities and hardnesses. It will be understood that, unless specifically mentioned otherwise, by "oil" or "wax" is meant the physical appearance and handling characteristics of the material rather than a strict chemical definition of the composition.

Thus, nontoxic, resorbable materials that are flowable and/or malleable are highly desirable for a wide range of medical and surgical applications. These materials may be used for a large variety of purpose, including, without limitation, as a hemostat in stopping bleeding tissue and bone wounds; as carrier or matrix for bioactive or inert particles and drugs by a variety of modes of administration, for example orally, or as applied directly to bone or other tissues during surgery to promote healing; as a barrier to prevent adjacent tissue surfaces from sticking together, or to prevent the movement of fluids away from or into tissues; as a lubricant to facilitate the insertion or positioning of devices such as catheters or other implantable devices, as an adhesive putty to keep devices and materials in position during a procedure, and as resorbable coating materials for implants and medical devices.

For example, such a material may be useful in surgery as a bone wax or bone hemostatic composition. Traditionally, bone waxes are made from beeswax mixed with a softening agent such as paraffin to mechanically stem blood flow from bone bleeding; the bone wax is usually smeared across the bleeding edge of the bone, blocking the holes and causing immediate bone hemostasis through a tamponade effect.

However, there are a number of adverse effects inherent in traditional bone wax compositions. Paraffin-based bone wax is not absorbed by the body and thus remains are the site of application indefinitely. Furthermore, traditional paraffin-based bone wax inhibits new bone osteogenesis and acts as a physical barrier preventing bone union, even after it is removed from the site following surgery. Its use is therefore not indicated if bone growth or fusion is desired following surgery.

Substitutes for bone wax have been suggested as an attempt to circumvent these disadvantages; these suggested substitutes include, without limitation, hydrogels, gelatin paste, collagen, fibrin-collagen paste, and bioerodible polyorthoester, among others.

Hydrogels are generally well suited for use in contact with body tissues, having good biocompatibility, low toxicity, and solubility. However, the physical and mechanical properties of hydrogels are generally less than optimal for applications that require even small amounts of manipulation during their use. Crosslinked hydrogels are more elastic than non-crosslinked hydrogels but are not malleable because their gel structure is chemically bonded. Once cured, crosslinked hydrogels are substantially incapable of being molded or manipulated. Exposure to a force beyond the elastic limit of the hydrogel will result in fracture of the gel rather than plastic deformation.

Non-crosslinked hydrogels are formed by hydrophobic or electrostatic interactions. Since the bonding is reversible, such gels may exhibit malleable or flowable properties. In general, these types of materials are a soft gel with low elasticity and resiliency due to the weakness of the bonding force, and they are substantially incapable of being molded. In addition, the stability of certain drugs and bioactive compounds may be compromised in the presence of water. This further limits the applications of hydrogel based carriers.

Petroleum jelly and paraffin wax derived from petroleum, or from plant or animal origin, have suitable mechanical and physical properties for use as malleable, putty-like matrices, coatings, implants, lubricants and barriers. Depending upon the molecular architecture and average molecular weight, the material properties can range from soft flowable gel, gum, malleable soft wax, brittle hard wax, to soft plastics. Unfortunately, these substances are hydrophobic, insoluble in water and, as stated above, cannot be resorbed, metabolized or otherwise removed by the body. In the long run, this type of material may cause inflammation and interfere with wound healing.

Mixtures of hard wax materials, such as beeswax and carnauba wax which are esters of long chain alkanes, have been utilized as bone hemostatic agents. Bleeding from bone cannot be stopped by the same techniques used for soft tissues, such as by applying hemostatic clamps or electrocautery as bone is a rigid structure with a rich blood supply that circulates through a system of canals within the hard mineralized matrix, and extensive network of vessels within the bone marrow. A beeswax formulation applied to the cut surface stops the bleeding very effectively by adhering to the bone and physically occluding the open blood vessels. However, the beeswax remains at the application site long after the surgery, and may cause inflammation, granuloma formation, and interferes with bone healing. As a foreign body, the residual wax may also become a focus of persistent bacterial infection.

It is one object of the invention to provide an alternative to wax- and grease-based materials and methods their preparation for use in medical, dental, pharmaceutical, veterinary, and surgical applications that overcomes the known deficiencies of existing materials.

Porous implant materials are useful for the repair, augmentation and/or reconstruction of the bony skeleton including cartilage. Tissue ingrowth occurs in implants with interconnecting pores, for example, pores of 60 microns or greater average diameter. Porous implants may be made by sintering small particles or beads of a fusible material such as polyethylene or metal. An alternative way to make a porous material is to blend pore forming agents into a molten substrate, which is then cooled. The pore forming agents may then be removed to produce a porous structure.

The surface of highly porous implants is rough, abrasive and exhibits a high coefficient of friction when in contact with tissues. It can therefore be difficult to move porous implants into position during surgery. Moreover, the implant surface tends to collect debris such as fat and cellular material which can later become necrotic and harbor infection. By filling and covering the pores with a resorbable, biocompatible material, the surface roughness can be reduced without compromising the porosity of the material. Therefore, another object of this invention is to provide a porous implant in which the pores are filled or covered with a resorbable substance that is water-soluble and becomes lubricious when wet, resulting in an implant with a smooth surface, without cavities in which debris can become trapped, and with a lubricating layer which helps the surgeon to slide the implant through tissue planes during placement.

Both porous and non-porous granular devices (such as implants) may be used as a scaffold for tissue ingrowth after implantation into a surgical created defect site. The devices can be made from a broad range of natural and synthetic implantable substances, including particles comprised of, but not limited to, native autogenous bone or cartilage, bone or cartilage from cadavers, collagen, hydroxyapatite, bioactive glass, polymethylmethacrylate (PMMA), polytetrafluoroethylene (PTFE), polyethylene, and dimethylpolysiloxane. The performance of particulate (such as porous) implants is markedly improved by the addition of a matrix to temporarily bind the particles together, and to form putty that serves to improve the handling characteristics and to act as a delivery system. Thus, another object of the present invention is to provide a binder or a matrix for particulate implant materials to improve their handling performance.

Collagen, in the form of gelatin solution has been used as a medium for injectable compositions. For example, ARTEPLAST® from Rofil Medical International is an injectable material comprised of microspheres of poly-methylmethacrylate (PMMA) suspended in a gelatin solution, and ARTE-COLL® a product currently available in Europe and Canada, is comprised of smooth PMMA spheres, at a concentration of 25% PMMA/75% collagen by weight with 0.3% lidocaine suspended in bovine collagen. Following implantation, the gelatin is resorbed and replaced by native collagen. However, bovine collagen carries the risk of an immunogenic reaction by the recipient patient, and a potential risk of disease transmission (such as bovine spongiform encephalopathy) from infected bovine, and is not a desirable matrix for allograft bone.

U.S. Pat. No. 5,073,373 discloses the use of glycerol as a matrix for demineralized allograft bone in the form of a gel. For example, GRAFTON® from Osteotech is a simple mixture of glycerol and lyophilized, demineralized bone powder. GRAFTON® works well to allow the surgeon to place the allograft bone at the site. But glycerol is very soluble in blood, and has very low viscosity at body temperature. This causes the allograft bone particles in a glycerol matrix to flow away from the site almost immediately after placement, preventing the proper retention of the allograft bone within the defect site. Moreover, glycerol is toxic and irritating to the surrounding tissues.

U.S. Pat. No. 4,191,747 discloses a bone defect treatment with fat free, denatured bone meal powder. The bone meal is mixed with a polysaccharide in a solution of saline and applied to the bone defect site. U.S. Pat. No. 5,290,558 discloses a flowable, demineralized bone powder composition using an osteogenic bone powder mixed with a low molecular weight polyhydroxy compound from 2 carbons to about 18 carbons in chain length including sugars of different molecular architecture such as monosaccharides, disaccharides, water-dispersible oligosaccharides, and polysaccharides.

U.S. Pat. No. 5,356,629 discloses methods of making a bone cement to fill defects in bone by mixing biocompatible particles, such as PMMA coated with polyhydroxyethylmethacrylate in a biopolymer matrix (e.g., hyaluronic acid) to obtain a moldable semisolid mass. The biocompatible particles can be derived from xenograft bone, homologous bone, autogenous bone, as well as other synthetic substances. The bioactive substance can also be an osteogenic agent such as demineralized bone powder, in addition to morselized cancellous bone, aspirated bone marrow, and other autogenous bone sources.

Poloxamer-based thermo reversible hydrogels are being developed for use as a drug delivery system. The drug-containing Poloxamer solution is liquid at less than 10° C. After administered to the desired location in the body, the drug-containing solution forms a hydrogel as it warms to 37° C. The solidified gel remains at the site, slowly releasing the drug by diffusion and/or gradual dissolution of the gel matrix.

U.S. Pat. No. 6,281,195 discloses a Poloxamer hydrogel matrix for the delivery of osteogenic proteins. In particular, Poloxamer 407 (PLURONIC® F127) is used in the form of a hydrogel. Overall, the hydrogel based system including Poloxamer hydrogel, hyaluronic hydrogel, and polysaccharide hydrogel all exhibit high hydrophilicity, low adhesion to tissue, and low binding capacity for hydrophobic drugs, thus significantly limiting their applications.

U.S. Pat. Nos. 7,553,913, 7,829,616, 8,124,687 and International Patent Application PCT/US2004/004174 teach the use of alloys of alkylene oxide block copolymers and random alkylene oxide copolymers for medical applications. Random alkylene oxide copolymers, such as PLURACOL® V10 from BASF, are highly hydrophilic. Thus, the alkylene oxide copolymer and the random alkylene oxide copolymers have overall hydrophilic properties. Compositions prepared according this invention tends to exhibit faster material solubility, and low binding capacity for hydrophobic medicinal ingredients.

U.S. Patent Publication No. 2009/0286886 teaches resorbable polymer compositions comprised of a poly(alkylene)-poly(ethylene glycol) copolymer and a poly(alkylene glycol) polymer or copolymer for use in medicine, dentistry and surgery. Poly(alkylene)-poly(ethylene glycol) copolymers and their properties are relatively unknown and unproven for use in the medical implant field.

Reverse phase Poloxamer hydrogel, Poloxamer 407 (PLURONIC® F127) has been reported as anti-adhesion barrier for preventing tissue adhesions after reproductive surgery.

See Steinleitner A. et al., *Poloxamer 407 As An Intraperitoneal Barrier Material For The Prevention Of Postsurgical Adhesion Formation And Reformation In Rodent Models For Reproductive Surgery* OBSTET GYNECOL. 77(1):48-52 (January 1991). Various crosslinked hyaluronic acid, or hyaluronic acid-based materials have also been disclosed as anti-adhesion barriers as summarized in U.S. Patent Publication No. 2004/0013714. Overall, the hydrogel based anti-adhesion barriers exhibit low adhesion to tissue due to high hydrophilicity and high water content. The reverse phase Poloxamer hydrogel has no covalent cross-linking and dissolves too quickly into solution, providing insufficient anti-adhesion protection, while the crosslinked hydrogels requires costly synthesis for the preparation and purification of purified crosslinked hydrogel, and the biocompatibility of the purified product is not fully characterized.

Thus, another object of this embodiment of the invention is to provide a biocompatible and substantial anhydrous jelly-like material that are sticky, less water soluble, and is economical to manufacture for use as anti-adhesion barrier.

Copolymers of oxyethylene and oxypropylene have been proposed as materials to be used as a substitute for bone wax. See e.g., Provisional U.S. Patent Application Ser. No. 61/162,347. Examples of such copolymers include Poloxamers (such as surfactants sold under the name PLURONIC®), meroxapols (such as surfactants sold under the name PLURONIC® R), polyoxamines (such as surfactants sold under the name TETRONIC®), and the PLURACOL® surfactants.

Levy et al. (U.S. Patent Publication 2003/0095945 and provisional U.S. Patent Application No. 60/162,347) discloses methods and compositions for bone hemostasis comprising a sterile copolymer comprises a mixture of PLURONIC® polyoxyethylene-polyoxypropylene-polyoxyethylene triblock copolymers for use as a bone hemostasis agent. The application of alkylene oxide block copolymers over the bleeding sites of the bone for hemostasis was described. Claimed advantages over prior art methods include the finding that bone growth was not inhibited, and the water-soluble composition was resorbed and excreted. The preferred material described is a 9:1 blend by weight of two block copolymers: Poloxamer 235 (PLURONIC® P85) and Poloxamer 238 (PLURONIC® F88).

However, the material prepared according to Levy et al. is suboptimal in malleability for use as bone wax. In addition, after the copolymers were made molten, mixed and dissolved at 80° C., the compositions are plunged into liquid $N_2$ (boiling point $-196°$ C. and freezing point $-210°$ C.) to avoid such crystallization from occurring. The use of liquid $N_2$ to snap cool the material causes significant condensation around the working environment, and its use is hazardous and impractical for application in the production of implantable devices due, for example, to possible splashing and spattering of the liquid $N_2$. The formulations of bone hemostasis agents in the prior art lack one or more of the following attributes: biocompatibility, superior handling characteristics, and easy manufacture and storage as disclosed subsequently by some of the same inventors in Int'l Patent Application PCT/US2004/004174.

Wellisz et al., (U.S. Pat. No. 7,553,913 and Patent Publications No. 2009/0238758, 2006/0100370 and 2006/0140904), based on a later application by some of the same inventors of the '945 publication, discusses compositions comprising a) a random copolymer of a polyethylene oxide and other alkylene oxides and b) a non-random polymer comprising one or more poly(alkylene oxide), such as homopolymers and/or block co-polymers. As disclosed in these publications, polymer blends were formulated at 80° C. and the molten polymer blends were molded by casting in small molds and rapidly cooling the molds and composition at 4° C. until fully set (less than 5 minutes).

Fisher et al., (U.S. Patent Publication No. 20090286886) discusses resorbable polymer compositions comprised of a poly(alkylene)-poly(ethylene glycol) copolymer and a poly(alkylene glycol) polymer or copolymer for use in medicine, dentistry and surgery.

None of the compositions disclosed herein possesses the unexpected properties of the present invention, which combines low toxicity, biocompatibility, superior bone hemostatic activity, and controlled dissolution with further characteristics including broader utility, substantially enhanced malleability, adhesion, cohesion, and batch-to-batch uniformity compared to prior art compositions.

In another embodiment it is yet another object of this invention to provide a nonhydrogel polymer matrix for certain materials used in medicine, dentistry, and surgery, including, without limitation, bone particles, bioactive agents (including, without limitation, glasses) and drug components which provides a superior combination of adhesive and cohesive properties, ease of handling, optimal retention time at the site of application, minimal swelling, and which is made from nonbiological compounds and is manufactured and used in an essentially anhydrous state.

SUMMARY OF THE INVENTION

In a major embodiment the present invention concerns compositions comprising a versatile, biocompatible polymer that includes a microcrystalline component substantially dispersed within an amorphous component. By "biocompatible" means that the composition is substantially non-cytotoxic, does not generate any substantial amount of toxic metabolites in humans, does not inhibit bone osteogenesis and are suitable for medical and/or implantable applications. Very preferably, the microcrystalline component has a hydrophilic property and the amorphous component has a hydrophobic component, although in other preferred embodiments this relationship may be reversed. The viscosity and thus the phase (e.g., liquid, paste or gel, or solid) of the composition may be tailored to the desired use of these compositions. In preferred embodiments such compositions of the present invention have one or more property making the composition particularly suitable for uses including, without limitation, medical, dental, pharmaceutical and surgical uses. Methods of making and using the composition and related products are also included within the present invention.

The present invention results from the unexpected discovery that cooling and substantially solidifying a molten alloy of non-random copolymers containing hydrophobic and hydrophilic side chains slowly rather than rapidly permits the crystallization of the hydrophilic component within the molten alloy. At the same time, this process permits the resulting microcrystals to be dispersed within and surrounded by the hydrophobic moieties of the polymer chain, thus giving rise to softer, more "workable", malleable, adhesive and cohesive materials than those made with identical ingredients but cooled more rapidly. Moreover, even the gross characteristics of such materials, such as the surface of the materials, the formation of cracks and breakage of molded versions of the material, are visibly different and superior to those made by methods involving "flash" or rapid cooling. The claimed compositions and methods for making and using such products, and related products, according to such a process and for such applications have not previously been reported.

By "alloy" is meant a macroscopically homogeneous mixture of polymers blended while each polymer is in a molten state.

This observation and subsequent characterization of the slowly cooled materials has resulted in the invention disclosed and claimed herein.

Thus, in one embodiment the invention may comprise a polymeric composition comprising a polymer microcrystalline embedded within amorphous matrix, and with properties that are ideally suited for numerous medical, dental, veterinary and surgical uses.

In further embodiments, the present composition may be a polymer alloy. The composition is very preferably biocompatible, and substantially non-toxic to living tissue. In a preferred embodiment the composition is substantially non-metabolizable, but readily eliminated from a body under physiological conditions; however in other embodiments the composition may be readily eliminated in unmodified form by the body, or substantially metabolizable under physiological conditions or any combination thereof.

The composition is preferably formulated to be water soluble. However the composition may contain little or no water (i.e., substantially anhydrous except for minor amounts of absorbed water). As used herein, "substantially anhydrous" means less than 10% water by weight, or less than 5% water by weight, or less than 4% water by weight, or less than 3% water by weight, or less than 2% water by weight, or less than 1% water by weight.

The composition may have a consistency of from viscous oil to a hard wax, including a grease or paste. Water may be added prior to use or absorbed in the body, but it is preferred to formulate the composition as a substantially anhydrous malleable polymer alloy before use in the body or further formulation.

Very preferably, although not necessarily, the present invention is not considered a hydrogel, especially before use in the body or further formulation. In the event that the composition is made to contain water, it may nevertheless be formulated to include water from 10% by weight, or 15% by weight to 20% by weight, or from 10% by weight, 15% by weight, or 20% by weight, or 25% by weight to 30% by weight, or from 15% by weight, or 20% by weight, or 25% by weight, or 30% by weight or 35% by weight, to 40% by weight.

Thus, in preferred embodiments a composition of the present invention may be a polymer alloy comprised of one or more amphiphilic block copolymers. Preferably, the composition comprises of purified amphiphilic block copolymers that have been processed to remove the impurities, such as initiators, residual solvents, and/or low molecular weight polymer fractions, contained within the amphiphilic block copolymers. Purifications can be conducted by typical methodologies, such as, centrifugation, chromatography, super critical fluid extraction, etc. More preferably, the composition comprises at least two amphiphilic block copolymers. The amphiphilic, block copolymer can be a synthetic polymer, natural polymer or a polymer with a component derived from natural source, such as cellulose, chitosan, hyaluronic acid, polypeptide or other natural materials. In one preferred embodiment, the amphiphilic block copolymer is a synthetic, amphiphilic polyoxyalkylene block copolymer comprised of at least one poly(ethylene oxide) block. In another preferred embodiment, the composition may comprised of (i) at least one amphiphilic, block copolymer with a melting point greater than or equal to 37° C., and (ii) at least one amphiphilic, block copolymer with a melting point less than 37° C.

In another preferred embodiment, the amphiphilic block copolymer is a polyoxyalkylene block copolymer comprised of at least one poly(ethylene oxide) (PEO) block, and at least one poly(propylene oxide) (PPO) block. In yet another preferred embodiment, the amphiphilic block copolymer comprises a PEO-PPO-PEO triblock copolymer. Yet in another preferred embodiment, the amphiphilic block copolymer comprises a PEO-PPO-PPO-PEO tetra-block copolymer.

In addition to the identity of the amphiphilic block copolymer, formation of microcrystals is induced by the choice of specific, blending, molding and cooling conditions which allows the molten polymer or polymer blend to be cooled at or below a certain rate. When molten polymer is cooled slowly enough to permit the initiation of microcrystal formation, the resulting polymer has very unique properties compared to a composition made from the same ingredients in the same proportions but lacking the microcrystalline phase dispersed within and surrounded by the amorphous phase. Thus, the physical and chemical properties of such polymer alloys are significantly affected by microcrystalline formation.

In the compositions of the present invention choice of the nature of the alkylene oxide(s), identity of the hydrophobic and hydrophilic chains, side chain length, molecular mass, mass ratio, and the methods of manufacture can affect the resulting composition's properties: e.g., adhesiveness, cohesiveness, ductility, malleability, and hardness. For example, "working" the composition may change its characteristics by homogenizing its internal structure. Handling characteristics may be tailored to be similar when compared between ambient temperature (e.g., 20° C. to 25° C.) and body temperature (e.g., 37° C. to about 40° C.).

In a particular embodiment, the average molecular mass of the amphiphilic block copolymer ranges from about 1000 g/mol or about 2000 g/mol or about 2500 g/mol or about 3000 g/mol, or about 4000 g/mol, or about 5000 g/mol to about 100,000 g/mol, or to about 75,000 g/mol, or to about 50,000 g/mol, or to 25,000 g/mol. Other ranges are included within each of these possibilities, such as from about 1500 g/mol to about 10,000 g/mol, or about 11,000 g/mol, or about 12,000 g/mol, or about 13,000 g/mol, or more. The amphiphilic block copolymer may have a molecular mass of at least about 2 kg/mol, or at least about 4 kg/mol, or at least about 6 kg/mol, or at least about 10 kg/mol; the molecular mass may also be not more than about 10 kg/mol, not more than about 15 kg/mol, or not more than about 20 kg/mol, or not more than about 50 kg/mol.

Those skilled in the art will appreciate that the compositions described here may be utilized for a wide variety of applications. The present invention provides for one or more of water-soluble, biocompatible, substantially non-toxic, substantially non-metabolizable, and eliminated compositions. Compositions which are polymer alloys are preferred. A "polymer alloy" defined under the conditions described here is a composition of two or more different species of polymers which is comprised of compatible and miscible polymer blends, but this definition excludes incompatible polymer blends. In this context "compatibility" means that both polymers can be homogeneously mixed and dispersed with each other in macroscopic scale under the intended application conditions. Thus, compatible polymers will mix or disperse within each other during melt mixing and cooling without separating out, such as precipitating out from the polymer mixture. Not all of the amphiphilic block copolymers are compatible. Those that have substantially difference in molecular weight and/or molecular architecture are incompatible. For example, PLURONIC® F68 and L121 are incompatible in most proportions including compositions containing from 6 to 65 weight % of F68. During cooling, F68 PLURONIC® polymer simply precipitates or separates out from the molten mixture.

In a preferred embodiment, the compositions of the present invention comprise a polymer alloy having a plurality of microcrystallines substantially homogeneously dispersed and surrounded by an amorphous phase. The composition is a macroscopically homogeneous composition comprised of two or more different species of compatible and miscible polymer blends. Preferably the composition comprises hydrophobic and hydrophilic domains or moieties, for example, side chains in a block copolymer. The desired attributes and handling characteristics of the composition can be designed as shown herein by appropriate selection of polymers, their molecular masses and ratios, and the amount of microcrystallines in the polymer alloy.

For example, a composition of the present invention may be made by blending until homogeneous a mixture of polymers at a temperature sufficient to render each polymer in a molten state. The polymer blend is preferably comprised of (i) at least one amphiphilic block copolymer with a melting point greater than or equal to 37° C., and (ii) at least one amphiphilic block copolymer with a melting point or pour point less than 37° C.

The molten mixture is then cooled at a rate that induces the formation of microcrystals of at least one of the copolymer blocks of the polymer alloy. For example, the alloy may be mixed at 80° C., poured into molds and permitted to cool to room temperature. In one embodiment the molds may be incubated at 80° C. before the molten alloy is added; in another embodiment the molds may be at room temperature when the alloy is added. For alloys of PEO-PPO-PEO triblock copolymers, an average cooling rate over the first minute of cooling slower than about −15° C./min, or slower than about −25° C. per minute is generally sufficient to form microcystals in a molten material initially at about 80° C. at the initiation of molding or cooling.

In the prior art considerable effort is often made to prevent the crystallization of components of polymer blends when making surgical, dental, pharmaceutical and veterinary products comprising polymers and polymer alloys and blends; for example, by plunging the molten polymer into liquid nitrogen, by rapid cooling to 4° C., or pouring the alloy into molds that are pre-cooled to, for example, 4° C. or less. While not wishing to be limited by theory, it is thought that such rapid cooling prevents the seeding and growth of crystals within the composition as it becomes more viscous or solid. By contrast, the present invention involves promoting the growth and controlling the amount of microscopic crystals within the composition.

The amphiphilic block copolymer can be a synthetic polymer or a polymer derived from natural source, such as cellulose, chitosan, hyaluronic acid, polypeptide or other natural materials, or a synthetic polymer chemically modified with a polymer derived from natural sources, or vice versa. In one preferred embodiment, the amphiphilic block copolymer is comprised of at least one polyoxyalkylene block. In another preferred embodiment, the amphiphilic block copolymer is comprised of at least one poly (ethylene oxide) block. A particularly preferred block copolymer class is the PLURONIC® copolymers of oxyethylene and oxypropylene. In another embodiment, the PLURONIC® copolymers are chemically modified by grafting with a biologically or medically efficacious component.

Melt Point

The melt point of a wax or malleable polymeric material is the temperature at which the material liquefies. In general, the pour point is a higher temperature than the melt point. The pour point of a liquid is the lowest temperature at which it becomes semi solid and loses its flow characteristics. The melt point of a material can be determined by observing the phase change of the material using a thermometer. The thermal cooling profile of a molten material or the thermal warming profile of solid material can also reveal the phase transition as a result of the exotherm of crystallization or the endotherm of melt transition, respectively.

Degree of Crystallinity

The fraction of the ordered molecules in polymer is characterized by the degree of crystallinity, which typically ranges between 10 and 80%. Higher values are generally only achieved in materials having small molecules, which are usually brittle, or in samples stored for long time at temperatures just under the melting point. Due the molecular chain entanglement, polymers rarely form perfect crystalline regions. Most methods of evaluating the degree of crystallinity assume a mixture of perfect crystalline and totally disordered areas; the transition areas are expected to amount to several percent. These methods include density measurement, differential scanning calorimetry (DSC), X-ray diffraction (XRD), infrared spectroscopy and nuclear magnetic resonance (NMR). The measured value depends on the method used, which is therefore quoted together with the degree of crystallinity. In addition to the above integral methods, the distribution of crystalline and amorphous regions may be visualized with microscopic techniques, such as polarized light microscopy and transmission electron microscopy.

The presence of ordered and crystalline fractions in polymers can also be detected by the exotherm of the crystallization process, the endotherm of the crystal melting process and/or the differences in physical and/or mechanical properties between non-crystalline and crystalline-containing polymers. In such a case, the degree of crystallinity can be estimated from the amount of the exotherm, endotherm and the differences in physical and/or mechanical properties between non-crystalline and crystalline-containing polymers, respectively.

Factors Affecting the Degree of Crystallinity

In certain embodiments of the present invention, the degree of crystallinity is controlled or determined by the amount of the crystallizable polymer component. In general, a greater proportion of a crystallizable polymer component in a composition results in a higher degree of crystallinity. In certain embodiments of the present invention, the degree of crystallinity is determined or controlled by the cooling rate of the polymer melt; a slower cooling rate, in general, results in more microcrystalline formation. In certain embodiments of the invention, the amount of crystallinity is determined or controlled by controlling the physical parameters of molding and the cooling processing parameters that affect crystallization formation. For example, applying pressure or stress can increase microcrystalline formation, while agitation, such as blending, can impede microcrystalline formation.

In preferred embodiments, the degree of crystallinity of the biocompatible composition of the present invention ranges from 1% to 25%. In other embodiments, the degree of crystallinity of the biocompatible composition of the present invention ranges from 25% to 50%. In still other embodiments, the degree of crystallinity of the biocompatible composition of the present invention ranges from 50% to 80%. In certain embodiments, the degree of crystallinity of the biocompatible composition of the present invention ranges from 35% to 55%.

Poly(Alkylene Oxide)

Poly(alkylene oxide)s (PAO) which are also known as polyoxyalkylenes (POA) are made by the polymerization of alkylene oxides (e.g., ethylene oxide, propylene oxide, butylene oxide). A homopolymer is formed only from one type of alkylene oxide while a copolymer is formed from two or more different alkylene oxides, known as alkylene oxide copolymers (AOC). Examples of the former are poly(ethylene oxide) (PEO), which is a polymer of ethylene oxide (EO), and poly(propylene oxide) (PPO), which is a polymer of propylene oxide (PO). Poly(ethylene oxide) is also commonly known as polyethylene glycol (PEG) or polyoxyethylene (POE).

The molecular weight of such polymers is generally characterized as the average of a distribution of lengths (or repeat units). PEO is amphiphilic, extremely hydrophilic, water-soluble, biocompatible, and substantially non-toxic, and is produced commercially in a wide range of molecular mass (200 g/mol to 10 million g/mol). Low molecular mass forms of PEO below 600 g/mol (i.e., oligomeric forms with less than 14 EO monomer units on average) are low-viscosity liquids at room temperature; PEO is a solid at 25° C. above 600 g/mol. PPO differs from PEO in that it is hydrophobic, generally insoluble in water except at low molecular weights (less than about 1 kg/mol), and is liquid at 25° C. even at high molecular weights (e.g., 6 kg/mol). The homopolymer may have a molecular mass of at least about 1 kg/mol, about 2 kg/mol, or about 5 kg/mol; the molecular mass may also be not more than about 10 kg/mol, about 20 kg/mol, or about 50 kg/mol. The compound may be further described by intermediate ranges using the aforementioned upper and lower limits.

In addition to the standard linear forms, branched or star forms of poly(alkylene oxide)s are produced by initiating the polymerization reaction with a polyfunctional initiator with multiple hydroxyl-, amino-, or thiol-groups each of which can serve as a starting point for polymer chain growth. For example, the use of glycerol (three hydroxyl groups) as an initiator results in a three-armed branched polymer, while pentaerythritol results in a four-armed polymer. PEO molecules of this type are available commercially (e.g., the Sunbright™ series, NOF Corporation, Japan) with anywhere from three to more than one hundred arms. Conventionally, polymers of this type with 3 to 10 arms are termed "branched" while those with more than 10 arms are termed "star" polymers. "Comb" copolymers are similar to branched and star forms, but the initiator for comb copolymers is a polyfunctional polymer with multiple hydroxyl-, amino-, or thiol-groups spaced along the initiator backbone, each of which can serve as a staring point for polymer chain growth. "Graft" copolymers are made by the addition of pendant polymer chains along a polymer backbone that possesses unsaturated C=C bonds or pendant functional groups (e.g., hydroxyl) from which pendant chains can be added by using a reactive monofunctional polymer chain.

All poly(alkylene oxide)s contain, in addition to multiple alkylene oxide-derived repeat units, a single residue corresponding to the molecule used to initiate the polymer synthesis. For linear polymers, this may, but need not, be an alkylene glycol corresponding to the alkylene oxide used for the synthesis (e.g., ethylene glycol and ethylene oxide, respectively) and thus the initiator-derived residue will be indistinguishable from the other repeat units in the polymer chain.

Small molecules other than alkylene glycols are often used as initiators, examples include methanol or N-butanol (for linear polymers) and trimethylol propane, glycerol, and pentaerythritol (for branched polymers) or ethylene diamine. The mass of initiator relative to the mass of the final polymer chain is generally very small and can usually be neglected. Thus, the term poly(alkylene oxide) is used here in its customary sense, and includes both poly(alkylene oxide)s initiated with an alkylene glycol molecule and poly(alkylene oxide)s initiated with another small molecule. Water-soluble poly(alkylene oxide)s are substantially non-toxic when applied to the skin or taken orally, and PEG and some Poloxamers (e.g., PLURONIC® F68 or Poloxamer 188) have been evaluated for medical and surgical applications, and demonstrated to be suitable for parenteral use.

Block Alkylene Oxide Copolymers (AOC)

Block alkylene oxide copolymers (AOC) may be linear or branched, and preferably have a molecular mass from about 1 kg/mol to about 100 kg/mol (i.e., average molecular mass of a distribution of polymers). AOC's may have a molecular mass of at least about 2 kg/mol, about 4 kg/mol, about 6 kg/mol, or about 10 kg/mol; the molecular mass may also be not more than about 10 kg/mol, about 15 kg/mol, about 20 kg/mol, or about 50 kg/mol. A preferred block AOC is a copolymer of ethylene oxide (EO) and $C_nH_{2n}O$, where n=3 to 6 (propylene oxide (PO) is preferred). The mass ratio of ethylene oxide to the other alkylene oxide(s) preferably is from about 5:95 to about 95:5. It may have a mass ratio of at least about 10:90, about 25:75, or about 40:60; the mass ratio may also be not more than about 60:40, or about 75:25, or about 90:10. The compound may be further described by intermediate ranges using the aforementioned upper and lower limits. Preferred embodiments use a block alkylene oxide copolymer with (1) a molecular mass from about 4 kg/mol to 20 kg/mol and an EO:PO mass ratio from 20:80 to 90:10 or (2) a molecular mass from about 6 kg/mol to 13 kg/mol and an EO:PO mass ratio from 30:70 to 80:20.

Other Block Copolymers

Other block alkylene oxide copolymers may comprise polyethylene oxide, polypropylene oxide, polybutylene oxide, polycaprolactone, polyhydroxyalkanoate, poly-3-hydroxyvalerate (PHV), poly-hydroxybutyrate (PHB), (poly(hydroxybutyrate-co-hydroxyvalerate)) (PHBV), poly(lactide), polyglycolide, poly(2-hydroxyethyl methacrylate), polymethacrylate, polypeptide, polyvinyl alcohol, polyethylenimine, polysaccharide, polyvinylpyrrolidone. The polyoxyalkylene copolymer preferably comprises polyethylene oxide and polypropylene oxide blocks. The preferred polymer or polymer mixture is capable of being melted into a homogeneous mixture at an elevated temperature above the melting point of the polymer or the polymer mixture.

Synthesis of Block Copolymer

Block copolymers are synthesized sequentially. First, a central block is commonly polymerized from one type of alkylene oxide (e.g., PO), then one or more outer blocks are added to the ends in a second polymerization step using another alkylene oxide (e.g., EO). Poloxamers (e.g., PLURONIC® copolymers from BASF) are linear A-B-A triblock copolymers of EO and PO having the general formula $(EO)_x$-$(PO)_y$-$(EO)_x$, where x, y are the average number of EO and PO monomer units, respectively, in the block. A hydrophobe of the desired molecular weight is made by the controlled addition of propylene oxide to the two-hydroxyl groups of propylene glycol; ethylene oxide is then added to sandwich the hydrophobic block between hydrophilic blocks. The hydrophilic blocks constitute from 10% to 80% by weight of the final molecule. Poloxamers are available in a range of molecular mass from 1,100 to 15,000 g/mol and PO:EO ratios of 9:1 to 2:8. Meroxapols (e.g., PLURONIC® R from BASF) are linear triblock copolymers similar to Poloxamers but with a reversed (B-A-B) structure and hence the general formula (PO)y (EO)x (PO)y. A hydrophile of the desired molecular weight is made by the controlled addition of ethylene oxide to ethylene glycol; propylene oxide is then added to create hydrophobic blocks on the outsides of the central hydrophilic block. The physical properties of block copolymers range from low-viscosity liquids to pastes or gels to waxy or solid, depending upon the precise combination of molecular weight and EO:PO ratio (higher molecular weight and higher EO proportion increasing the melting point). See Schmolka (J. AM. OIL CHEM. SOC., 54:110-116, 1977).
BASF Corporation's PLURONIC®

In BASF Corporation's PLURONIC® code, the alphabetical designation is derived from the physical form of the product at room temperature: L for liquids, P for pastes, and F for flake (solid) forms. In the numerical designation, the first digit (or the first two digits in a three numeral code) multiplied by 300 indicates the approximate molecular weight of the hydrophobe. The last digit multiplied by 10 indicates the approximate percentage (w/w) of the hydrophile in the PLURONIC® copolymer. Preferred block AOC's are Poloxamer 108 (PLURONIC® F38), Poloxamer 188 (PLURONIC® F68), Poloxamer 238 (PLURONIC® F88), Poloxamer 288 (PLURONIC® F98), Poloxamer 338 (PLURONIC® F108), Poloxamer 237 (PLURONIC® F87), Poloxamer 407 (PLURONIC® F127), Poloxamer 403 (PLURONIC® P123), Poloxamer 335 (PLURONIC® P105), PLURONIC® P103, PLURONIC® P104, PLURONIC® P85, and PLURONIC® L122.

Poloxamines (e.g., TETRONIC® block copolymers from BASF), are 4-armed symmetrical poly(alkylene oxide) block polymers prepared using an ethylene diamine initiator with the general formula $[(EO)_x-(PO)_y]_2-NCH_2CH_2N-[(PO)_y-(EO)_x]_2$, and are another example of an alkylene oxide copolymer that may be used to make the presently claimed compositions. Reverse poloxamines, in which the four PEO blocks are added before the four PPO blocks, can also be used. TETRONIC® R block copolymers, are 4-armed symmetrical poly(alkylene oxide) block polymers similar to TETRONIC® block copolymers but with a reverse $[(EO)_x-(PO)_y]$ structure.

In contrast, most random copolymers are synthesized non-sequentially by polymerizing two different types of monomers together. For example, equal amount of two different monomers may be mixed and polymerized together to form a random copolymer. In such a situation, the resulting sequence distribution of the monomer units in a polymer chain is dependent upon the reactivity of the type of monomers. If both types of monomers are substantially equivalent in reactivity, they will randomly add to the growing polymer chain and form random copolymer. The sequence distribution of the monomer units in the polymer chain is determined by the reactivity ratio of the two types of monomers, and can be ascertained by analytical methods, such as, infrared spectroscopy or nuclear magnetic resonance spectroscopy method.
PLURONIC® Applications Pharmaceutical and medical applications of PLURONIC® and PLURONIC® alloys are known and have been disclosed in the prior arts. These applications include, but not limited to, bone hemostasis agents, carriers for bone particles, carriers for bioactive agents, and carriers for therapeutic drugs. Compositions of, and made according to, the present invention can be used for such applications as well.

For example, Poloxamer 188 (PLURONIC® F68) (8350 g/mol, 80% POE), has been used for topical wound cleaning and has been approved for intravenous use as an emulsifier for perfluorocarbon oxygen-carrying formulations. Aqueous solutions of a Poloxamer such as Poloxamer 407 (PLURONIC® F127) (12,500 g/mol, 70% POE) at a sufficiently high concentration (i.e. greater than about 30% w/v) are used as hydrogel formulations for drug delivery. PLURONIC®-based micellar drugs in various stages of development have been and are being investigated as anticancer drugs for various illnesses.

Doxorubicin-loaded mixed micelles of PLURONIC® L61 and F127 are being evaluated in clinical trials in patients with advanced esophageal carcinoma. (Danson, S. et al., *Phase I Dose Escalation And Pharmacokinetic Study Of PLURONIC® Polymer-Bound Doxorubicin (SP1049C) In Patients With Advanced Cancer*, BR. J. CANCER (2004) 90, 2085-2091).

Paclitaxel-loaded PLURONIC® P123/F127 mixed micelles are being developed for use against metastatic breast cancer and refractory ovarian cancer. Drugs loaded in PLURONIC® micelles result in increased solubility, metabolic stability, and improved circulation time, thus significantly increasing drug's safety and effectiveness.
Biological Response Modifiers Certain block copolymers of polyalkylene oxide alone, without additional drugs associated, have been demonstrated to affect or influence cellular activities. These copolymers exhibit many beneficial medicinal applications, including cellular repair, chemosensitizing activity and enhancing drug delivery across blood-brain barrier. For example, PLURONIC® F68 (Poloxamer 188), has been demonstrated to exhibit cellular repair capability. This block copolymer has the ability to insert itself into damaged cellular membranes, allowing for the stabilization and repair of the membrane to take place. Afterwards, the block copolymer is released from the repaired cells and excreted from the body.

PLURONIC® block copolymers, such as PLURONIC® P85, are known to sensitize multidrug resistant (MDR) tumors with respect to various anticancer agents, particularly, anthracycline antibiotics. Cells displaying high responses in ATP depletion were strongly sensitized by the block copolymer resulting in drastic increases of doxorubicin cytotoxic activity. See Kabanov A. V., Batrakova E. V., & Alakhov V. Y., *An Essential Relationship Between ATP Depletion And Chemosensitizing Activity Of PLURONIC® Block Copolymers*, J. Control Release 2003 Aug. 28; 91(1-2):75-83.

In addition, PLURONIC® P85 was also shown to enhance the delivery of digoxin to the brain through the inhibition of the P-glycoprotein-mediated efflux mechanism. (Batrakova E. V., Miller D. W., Li S., Alakhov V. Y., Kabanov A. V., Elmquist W. F., *PLURONIC® P85 Enhances The Delivery Of Digoxin To The Brain: In Vitro And In Vivo Studies*, J. PHARMACOL EXP THER. 2001 February; 296(2):551-7.

The biological activity of PLURONIC® surfactants is related to their ability to incorporate into membranes, followed by subsequent translocation into the cells and affecting various cellular functions. As a result, PLURONIC® surfactants cause drastic sensitization of MDR tumors to various anticancer agents, enhance drug transport across the blood brain and intestinal barriers, and causes transcriptional activation of gene expression both in vitro and in vivo. It was found that the biological effects of PLURONIC® surfactants are most effective at the unimer level. Above the CMC, PLURONIC® surfactants appear to associate into micelles and exert little biological effects. These studies demonstrate that PLURONIC® surfactants have a broad spectrum of biological response modifying activities, which make them a very potent drug targeting system.
Micellar Drugs Micelles of polyalkylene block copolymers, such as those prepared from PLURONIC® P105 and from PLURONIC® P123, and co-micelles prepared from PLURONIC® L61/

F127, and from PLURONIC® P123/F127 have been employed as carriers for anti-cancer drugs. These polymeric micelles have a core-shell structure which enables the system to incorporate poorly soluble drugs and protect from inactivation in biological media. Due to their small particle sizes (<200 nm), these systems exhibit many advantages such as bioavailability, targeting ability, long circulation and easy production on effective delivery of drugs. See Zhang Wei, et al., *Paclitaxel-Loaded PLURONIC® P123/F127 Mixed Polymeric Micelles: Formulation, Optimization And In Vitro Characterization* INT. J. PHARM. 376:176-185 (2009).

The capability of PLURONIC® amphiphilic block copolymers to exert beneficial biological effects coupled with their capability to form micellar-drug formulation can significantly increase the safety and effectiveness of drug application by using a substantially lower drug dose. For example, one can formulate micellar or mixed micellar drug comprising appropriate amounts of PLURONIC® biological response modifier, such as P85 or L61, using high molecular weight PLURONIC®, such as P123 and F127 that exhibits high micellar stability and drug loading capability, but with little or no biological response modification effects. Administered at micellar concentrations above the critical micellar concentration (CMC), PLURONIC® micellar drug formulations disintegrate upon dilution in the blood stream, releasing both the drug and PLURONIC® biological response modifier to synergistically accomplish the therapeutic effects.

Stability of Micellar Drugs

Micellar drug formulations of the present invention can be prepared by melting and mixing the drug compounds together with the desired polymeric carriers and then cooling the mixture in accordance with the present invention to form a drug-containing microcrystalline matrix. Alternatively, they can also be prepared by dissolving a mixture of drug and the desired polymeric mixture in a solvent. After filtration and evaporation of the solvent, the solid drug/polymer mixtures can be melted and cooled in accordance with the present invention to form a drug-containing crystalline matrix that can release micellar drugs. The drug-containing crystalline matrices prepared as above can be reconstituted and sterile filtered before administration.

The stability of the drug-containing matrix is of high importance in the development of micellar-drug formulation, as this may determine the shelf life and the effectiveness of the drug. It has been reported that the drug content in drug-containing micelles may vary due to poor matrix stability. Current micellar drugs are stored in lyophilized powders before reconstitution for administration. However, the drug molecules in the drug-containing lyophilized powders may gradually aggregate during storage, thus affecting the dosage and stability of micellar drugs.

The drug-containing crystalline matrices prepared according to the present invention present multiple advantages. For example, the presence of microcrystallines in the drug-containing matrix can freeze the drug-containing matrix and prevent drug molecules from migration and aggregation during storage. In another advantage, the presence of microcrystallines stabilizes the drug-containing matrix at a lower energy state, enhancing the stability of the drug-containing matrix. In a further advantage, the presence of microcrystalline requires additional energy and time for the sterile water or body fluid to solvate and dissolve the microcrystals in order to release the drug-containing micelles, thus stabilizing and extending the drug release profile.

Applications of PLURONIC® F127 Aqueous Gels

Block copolymers of polyalkylene oxide have also been found useful in several other pharmaceutical formulations. As a non-limiting example of the applicability of certain embodiments and aspects of the invention, the characteristics of a specific block copolymer, PLURONIC® F127, is exemplified. PLURONIC® F127 has been extensively evaluated as a carrier for active pharmaceutical ingredients.

The PLURONIC® F127 is typically used as an aqueous gel with a concentration ranging from 25% by weight to 35% by weight in aqueous solution. The concentration of PLURONIC® F127 in the aqueous gel is limited by the PLURONIC® F127's solubility and ability to form a gel. At this concentration range, PLURONIC® F127 behaves as a reverse phase medium: i.e., the aqueous gel is a liquid at, or below freezing temperature, but become a gel at, or above room, or body temperature. This reverse gelation phenomenon facilitates the delivery and the control sustained release of pharmaceuticals. The drug release rate of such a formulation is controlled by the rate of dissolution of the PLURONIC® F127 gel. While PLURONIC® reverse gels have been found useful in many applications, they suffer from two disadvantages: (A) high water content, and (B) high hydrophilicity.

By contrast, in certain embodiments the present invention provides a preferably substantially anhydrous and less hydrophilic PLURONIC® polymer alloy comprising microcrystalline moieties dispersed within and surrounded by an amorphous hydrophobic phase that can be made with a consistency similar to the PLURONIC® F127 reverse phase gel.

Carrier of Bone Particles, Bioactive Agents and Therapeutic Drugs

The composition of the present invention can also be used as a carrier for bone graft and/or soft tissue graft particles, including polyethylene particles, hydroxyapatite particles, ceramic particles, bioactive glass particles, bone fragments, bone powder, and demineralized bone particles.

The present composition can also be used as a carrier for bioactive agents, such as antibodies, antigens, bone growth factors, chemokines, cytokines, demineralized bone matrix, enzymes, hormones, morphogenic proteins, nucleic acids, receptors, ligands, biological response modifier, and signaling molecules.

In addition, the present composition can also be used as a carrier for therapeutic drugs, such as, analgesics, anesthetics, antigens, antibiotics, anti-infective drugs, steroidal and non-steroidal anti-inflammatory drugs, imaging and contrasting agents, bone growth factors or morphogenic proteins, photo sensitizing agents, radiotherapeutics and chemotherapeutics drugs.

Bioactive agents and therapeutics that can be carried by a solid carrier have been disclosed in the prior art. For example, U.S. Pat. No. 6,923,988 discloses many bioactive agents for use in various therapeutic categories including, analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxioytic agents, sedatives, hypnotics, neuroleptics, β-blockers, cardiac inotropic agents, corticosteroids, diuretics, anti-parkinsonian agents, gastro-intestinal agents, histamine receptor antagonists, kerarolytics, lipid regulating agents, anti-anginal agents, Cox-2 inhibitors, leukotriene inhibitors, macrolides, muscle relaxants, nutritional agents, opioid analgesics, protease inhibitors, sex hormones, stimulants, muscle relaxants, anti-osteoperosis agents, anti-obesity agents, cognition enhancers, anti-urinary incontinence agents, nutritional oils, anti-benign prostate hypertrophy agents, essential fatty acids, non-essential fatty acids, and mixtures thereof. Specific examples of compounds that can be formulated with a solid carriers are also provided in this prior art. Each and every compounds cited or referenced in this patent application is individually incorporated herein by reference in its entirety.

Bioactive agents useful in the present invention may include, without limitation, any of the following compounds or drugs, including combinations of agents:

Retinoids, prostaglandins, protein kinase inhibitors (such as tyrosine kinase inhibitors), α- or β-adrenoreceptor agonists or antagonists, dopaminergic agonists, cholinergic agonists, carbonic anhydrase inhibitors, guanylate cyclase activators, cannabinoids, endothelin, adenosine agonists, anti-angiogenic compounds, angiostatic compounds, and neuroprotectants.

More specifically, the bioactive agent may include non-steroidal anti-inflammatory drugs (NSAIDs), analgesics, or antipyretics; antihistamines, antibiotics, beta-blockers, steroids, such as corticosteroids, anti-neoplastic agents, immunosuppressive agents, antiviral agents, and antioxidants.

Non-limiting examples of non-steroidal anti-inflammatory, analgesics, and antipyretics, include aspirin, acetaminophen, ibuprofen, naproxen, diclofenac, etodolac, fenoprofen, indomethacin, ketoprofen, oxaprozin, piroxicam, sulindac, diflunisal, mefenamic acid, and derivatives thereof.

As used herein, the term "derivative" refers to any substance that is sufficiently structurally similar to the material that it is identified as a derivative so as to have substantially similar biological or medical functionality or activity, for example, therapeutic effectiveness, as the material when the substance is used in place of the material. The functionality of any derivative disclosed herein may be determined using conventional routine methods well known to persons of ordinary skill in the art.

Neuroprotective compounds include, without limitation, (R,S)-alpha-methyl-4-carboxyphenylglycine, (S)-2-amino-4-phosponobutyrate, (2S,3S,4S)-alpha-carboxypropyl-glycine, (1S,3R)-1-aminocyclopentane-1,3-dicarboxyleic acid, nimodipine, nicardipine, ziconotide, dizocilpine, eliprodil, cerestat, D(-)-amino-5-phosphonopentanoic acid, selfotel, (+,-)-6-(1(2)H-tetrazol-5-yl)methyldecahydroisoquinoline-3-carboxylic acid, cis-(+,-)-4-[(2H-tetrazol-5-yl)methyl]piperidine-2-carboxylic acid, memantine, remacemide, dexanabinol, sinnabidiol, [2,3-dioxo-7-(1H-imidazol-1-yl)6-nitro-1,2,3,4-tetrahydro-1-quinoxalinyl]acetic acid monohydrate, 7-chloro-3-methyl-3,4-dihydro-2H-1,2,4-benzothiadiazine S,S-dioxide, GV150525A, 1-aminocyclopropanecarboxylic acid, ACPCM, ACPCE, R(+)-3-amino-1-hydroxypyrrolid-2-one, R-cis-β-methyl-3-amino-1-hydroxypyrrolid-2-one, ifenprodil, NPS-1506, 1,2-dihydophthalazine, licositnel, clomthiazole, MDL-27192, ceresine, ascorbic acid, nitroarginine, lubeluzole, steroidal anti-inflammatories, non-steroidal antiinflammatories, alpha-phenyl-n-t-butyl-nitrone, AEOL 10150 or 10113 metalloporphirin, L,L isomer of Z-Leu-aminobutyric acid-CONH(CH$_2$)$_2$, AK295, Z-Leu-aminobutyric acid-CONH(CH$_2$)$_3$-morpholine, N-benzyloxycarbonyl-Val-Phe, z-VAD-CHO, z-DEVD, citicoline, TAK-147, etanercept, LY-287041, atropine and pralidoxime.

Examples of antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, exbrompheniramine, methdilazine, and trimprazine doxylamine, pheniramine, pyrilamine, chiorcyclizine, thonzylamine, and derivatives of each of these agents.

Examples of antibiotics include, without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin, ofloxacin, gatofloxacin, moxifloxacin, clindamycin, metronidazole, gentamicin, lincomycin, tobramycin, vancomycin, polymyxin B sulfate, colistimethate, colistin, azithromycin, augmentin, sulfamethoxazole, trimethoprim, and derivatives thereof.

Examples of beta blockers (β-adrenergic receptor antagonists) include, without limitation, timolol, acebutolol, atenolol, labetalol, metoprolol, propranolol, and derivatives thereof.

Examples of corticosteroids include, without limitation, cortisone, prednisolone, triamcinolone, flurometholone, dexamethasone, medrysone, loteprednol, fluazacort, hydrocortisone, prednisone triamcinolone, betamethasone, prednisone, methylprednisolone, triamcinolone acetonide, triamcinolone hexacatonide, paramethasone acetate, diflorasone, fluocinolone and fluocinonide, derivatives thereof, and mixtures thereof.

Examples of antineoplastic agents include, without limitation, adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppresive agents include, without limitation, cyclosporine, azathioprine, tacrolimus, and derivatives thereof.

Examples of antiviral agents include, without limitation, interferon gamma, zidovudine, amantadine hydrochloride, ribavirin, acyclovir, gancicylovir, valciclovir, dideoxycytidine, and derivatives thereof.

Examples of antioxidant agents include, without limitation, ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamylcysteine, quercitin, lactoferrin, dihydrolipoic acid, citrate, *Ginkgo Biloba* extract, tea catechins, bilberry extract, vitamins E or esters of vitamin E, retinyl palmitate, and derivatives thereof.

Other bioactive agents include, without limitation, squalamine, carbonic anhydrase inhibitors, protein kinase inhibitors, α1 and α2 adrenergic agonists, prostamides, prostaglandins, antiparasitics, antifungals, and derivatives thereof.

Composition and Medical Device

Microcrystalline compositions of the present invention can also be prepared in conjunction with a medical material, or medical device, such as, bone graft material, anchors, catheters, implants, plates, prostheses, screws, sutures, drug delivery device, surgical instruments, endoscope, stent, pacemaker and defibrillator using a variety of methods, such as dipping, coating, extrusion and/or insert molding. For example, malleable compositions containing bone graft particles can be prepared by mixing bone graft particles with the molten components of the present composition and molded/cooled at a pre-determined cooling profile to promote the formation of microcrystalline. Alternatively, the molten components of the present composition can be dispensed or injected into a mold cavity containing a bone graft material, a bone implant or a stent, then allow the molten composition to cool at a specific or pre-determined cooling rate or profile to control the amount of microcrystalline formation of the present composition. Similarly, bone implants, such as dental implants and joint implants can be coated with the present composition. The thickness and the amount of molded-on or coated-on microcrystalline-containing composition can be controlled by the design of the mold and cooling profile, etc. Medical devices, materials or instruments can also be dipped into a molten composition or a solution containing the formulation of the composition to form a coating, and allow the coating to cool at a pre-determined condition to promote the formation of microcrystalline.

The present invention provides alloys of polymers, including PLURONIC® block copolymers, which can be reproducibly and economically produced for medical applications in a practical manner that can be scaled up and adopted for commercial production. Previous methods of making alloys compositions have used liquid $N_2$ to prevent the formation of crystals of polyethylene oxide chains. We found the process is hazardous and cannot be reproducibly used to produce sufficiently malleable PLURONIC® alloy. In addition, certain materials prepared according to prior methods was found to be cytotoxic.

Newer alloy compositions are based on a mixture of PLURONIC® block copolymer and random PEO-PPO; see U.S. Pat. No. 7,553,913. Such compositions, however, suffer from the lack of sufficient hydrophobicity, resulting in fast dissolution and limited capacity to deliver hydrophobic bioactive substance, because the random PEO-PPO copolymer is hydrophilic. United States Patent Publication 2009/0286886, by the same inventors discloses a more hydrophobic composition than the compositions of the present invention, comprising (a) a poly(alkylene)-poly(ethylene glycol) copolymer, and (b) a poly(alkylene glycol) polymer or copolymers. This is, however, a relatively unknown and unproven composition for medical application, and is clearly different compositionally from the present invention, which does not involve the use of random copolymers.

As has been disclosed above, and in the examples that follow, Applicant has discovered that co-polymer alloys, such as PLURONIC® alloys, containing a microcrystalline component substantially contained within and surrounded by an amorphous component, ranging in form from grease, gel, semi-solid, malleable wax to hard wax, can be very reproducible produced from a wide range of copolymers, such as PLURONIC® copolymers, that are readily and/or commercially available. The microcrystalline containing polymer alloy exhibits novel, unexpected, better and beneficial properties for medical and non-medical applications than those produced from the same components, but rapidly cooled to avoid the formation of crystals. Moreover, the PLURONIC® alloys with the beneficial properties can be produced by a simple, yet practical process that can be easily adopted for commercial production using readily available molding tools and/or equipment. An exemplification of the methods and compositions of the invention, using PLURONIC® copolymers for the formation of alloys according to the present invention, is given in the examples provided.

Polymer Crystals

Polymer crystallization is a known process and is described in the literature, publications, and various other sources, such as in the Wikipedia entry entitled Crystallization of Polymers. In general, crystallization of polymers is a kinetic process associated with the partial alignment of their molecular chains. Polymers may crystallize upon cooling from the melt, mechanical stretching or solvent evaporation. During crystallization, the polymer chains fold together and form ordered regions called lamellae, which may compose larger spheroidal structures called spherulites. Crystal growth is achieved by further addition of folded polymer chain segments to the lamellae. In general, spherulites may have a size between about 1 and 100 micrometers. Crystallization from the polymer melt occurs when the temperature is below the melting temperature and above a temperature where polymer chains have sufficient mobility, such as the glass transition temperature. Higher temperatures destroy the molecular arrangement and below the glass transition temperature, the movement of molecular chains is frozen. Due to chain entanglement and limited chain mobility, formation of 100% crystals or perfect crystals within an ordered region has never been achieved. Thus crystallized polymers are also called "semicrystalline".

In this invention, the formation of ordered regions including lamellae and spherulites are referred to as microcrystalline. The amount and size of microcrystalline formed depend on the material cooling profile and other processing conditions.

Degree of Crystallinity

The fraction of the ordered segment in polymer is characterized by the degree of crystallinity, which can be estimated by different analytical methods and it typically ranges between 10 and 80%. Most methods of evaluating the degree of polymer crystallinity assume a mixture of perfect crystalline and totally disordered areas. However, the transition areas may amount to several percent. These methods include density measurement, differential scanning calorimetry (DSC), X-ray diffraction (XRD), infrared spectroscopy and nuclear magnetic resonance (NMR). The measured value depends on the method used, and is therefore quoted together with the degree of crystallinity. In addition, the distribution of crystalline and amorphous regions can also be visualized with microscopic techniques, such as polarized light microscopy and transmission electron microscopy.

The presence of ordered and crystalline fractions in polymers can also be detected by the exotherm of the crystallization process, the endotherm of the crystal melting process and/or the differences between the physical and/or mechanical properties of non-crystalline and crystalline-containing polymers. In such a case, the degree of crystallinity can be estimated from the amount of the exotherm, endotherm and the amount of differences in physical and/or mechanical properties between non-crystalline and crystalline-containing polymers, respectively.

Properties of Semicrystalline Polymers

The properties of semicrystalline polymers depend on the degree of crystallinity. In general, crystalline formation results in a harder and more brittle material, in particular if the microcrystallines are not homogeneous or evenly distributed. Thus, it is more difficult to produce high crystallinity polymers by molding due to cracking and molding defects. If, however, the microcrystallines are homogeneously formed and evenly dispersed within the amorphous phase, it may result in tougher and stronger material.

The size and shape of the spherulite and/or lamellae, and the gaps between the spherulite and/or lamellae may be affected by the cooling rate, the conditions of the molding or forming process, the block length of the crystallizable polymer segment, the nucleation agents employed (if any) and the number of nuclear sites occurred during cooling process. In certain embodiments of the present invention, the aggregation of spherulite and the size of spherulite do not cause gross phase separation and/or gross material inhomogeneity to the molded compatible materials). The spherulites may range in size from 50 nanometers or less to about 100 nanometers, to about 1 micron, to about 10 microns, to about 100 microns or more. The ordered lamella regions may range in size from less than 10 nanometers, to 100 nanometers, to 1 micron, to 10 microns, to 100 microns or more. Both the lamella and spherulites may range in size from 1 micron or less, to about 10 microns, to about 100 microns or more. The crystallized polymer segment preferably has a molecular mass greater than about 2500 grams per mole, or about 3000 grams per mole, or about 5000 grams per mole, or about 6000 grams per mole, or about 7000 grams per more, or about 8000 grams per mole, or about 9000 grams per mole or more.

Different block copolymers have different melting temperature and different crystallization characteristics, which can be empirically determined. Thus, the optimal cooling profile to initiate, promote and control the amount of crystallization to attain optimal polymer alloy performance depends upon the molecular structures of the block copolymers used and the applications of polymer alloy. By holding the polymer alloy at a certain "crystallizable" temperature or temperature range will increase the amount of crystals formed. In one embodiment of the present invention, the cooling profile is pre-determined, controlled and monitored by a computer controlled cooling system, instead of being cooled naturally by the surrounding environment.

While the cooling process to induce the microcrystalline formation is often conducted under static condition, it is known that other physical processes may also stimulate or interrupt the formation of crystalline during cooling. For example, applying high pressure may cause the polymer chains to fold into a more orderly and compact crystalline structure while agitation by blending, stirring, or extrusion may impede the formation of large crystalline domains. In addition, if a polymer melt is forced through, e.g., a nozzle, such as a nozzle that is used in making fibers and films, it creates tensile stress which partially aligns its molecules. Such alignment can stimulate the formation of crystallization along its axis and affect the material properties.

Thus, one can couple the method of the present invention with additional processes to fine tune and control the formation of polymer crystalline moiety, and the property of final material. For example, the cooling of the molten material may be conducted by extruding the material through a static mixing tube with tailored mixing elements to control the flow rate and the pressure of the extruded material. Thus in addition to control the cooling process, one can also control the pressure gradient and the material flow rate exerted on the molten material during the cooling and microcrystalline formation process.

Each and every patent, patent application, and publication cited or referenced in this patent application is individually incorporated herein by reference in its entirety.

The Examples that follow comprise specific embodiments of the present invention. However, the present invention is not limited only to the disclosure of these examples, but is defined solely by the claims that conclude this specification.

EXAMPLE 1

Mold Tooling Design

Figure 1:
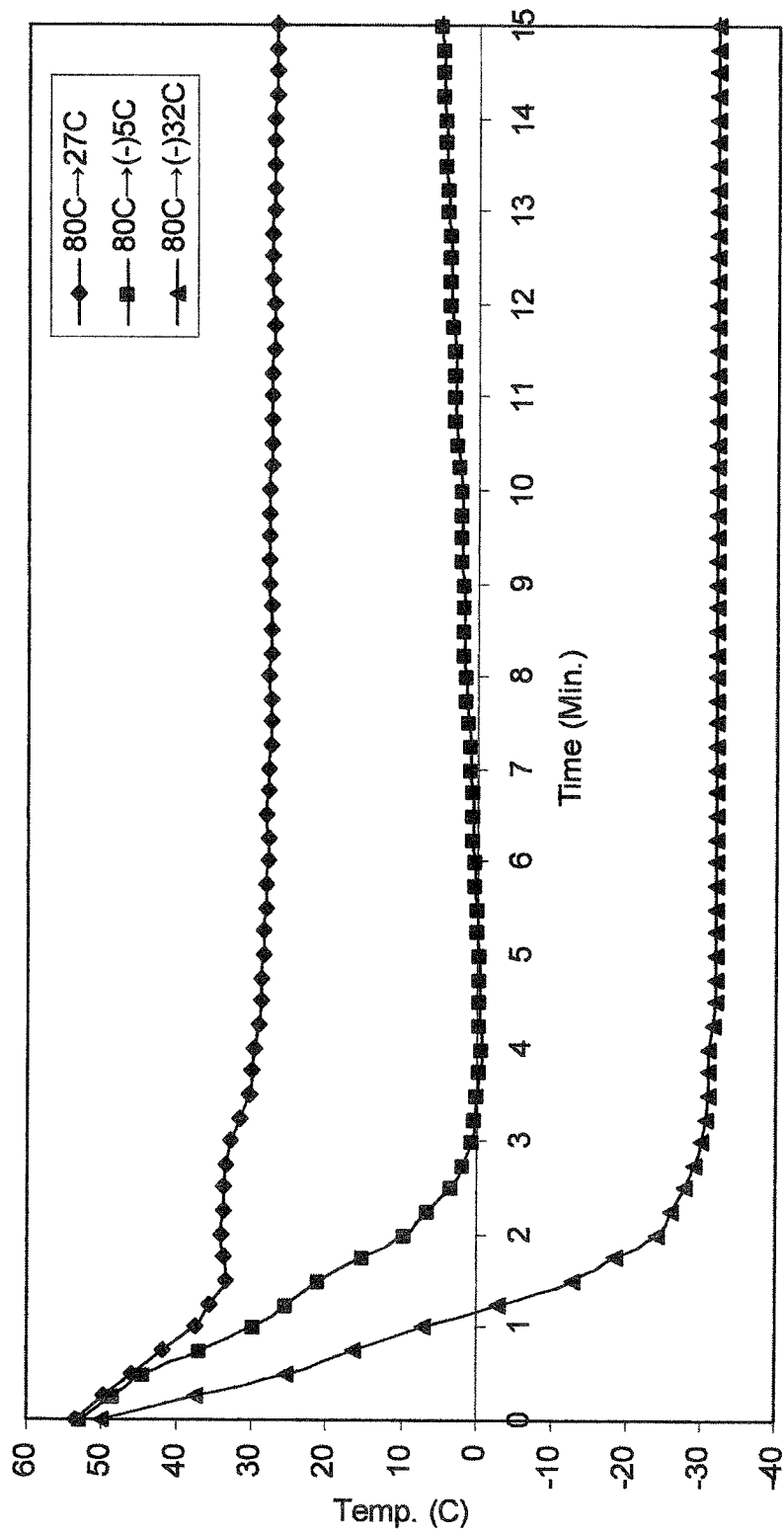
FIG. 1 is a plot of temperature versus time for the cooling profiles of 90:10 weight ratio of PLURONIC® P85 and F88 Blend prepared with different methods of cooling.

Our attempts to reproduce the bone wax hemostatic polymeric materials using the ingredients, proportions and process disclosed in U.S. Patent Publication 2003/0095945 and Provisional U.S. Application No. 60/162,347 (described above and incorporated by reference herein) were met with difficulty. First, it is awkward, hazardous and impracticable to employ liquid nitrogen, which has a boiling temperature of −196° C., to flash cool the molten polymeric material from its melting temperature. Second, the process is difficult to control and reproduce precisely, and very often produces molded polymeric material that is brittle, lacks cohesion, and is not sufficiently malleable for use as a bone hemostat.

In order to systematically study the cause and effects, a stainless steel mold tooling, comprising a 1.6 cm×7 cm×9.5 cm base plate, a ePTFE gasket, a 2 cm×7 cm×9.5 cm mold plate with 25 (5×5) cavities, each 8 mm in diameter and 20 mm in depth, equally spaced apart at 5 mm, along with a matching 25-pin demolding pin set, a digitally controlled heating platform and a thermal couple, were made and/or procured for the study. The mold tooling allows one to simulate commercial molding conditions and to produce consistent molded parts for evaluation. It also allows one to conduct design experiments to study the cause and corresponding effects.

In general, we have considered three major factors during molding:

(A) Mixing and dispensing. Here the key is to make sure that the material ingredients can be adequately blended and extruded, and can fill all the intricate cavities of the mold to form the molded articles.

(B). Cooling. Cooling may cause material shrinkage, crystallization, phase separation, void formation and/or cracks.

(C) Ejection. Molded articles have to be removed from the mold cavities without causing damage to the molded articles or leaving substantial residue on the mold surface.

The tooling described above allows one to produce compositions prepared in forms ranging from grease, semi-solid, wax, hard wax and solid. It also allows one to evaluate and compare these factors among different material formulations and processing conditions.

EXAMPLE 2

Preparation of PLURONIC® Alloys of P85 and F88 Blend

Two molten material temperatures (80° C. and 58° C.), three mold temperatures (room temperature (27° C.), −5° C. and −32° C.), and three different formulation weight ratios, 90:10, 80:20 and 70:30, of PLURONIC® P85 and F88 materials, respectively, were used in this study. The ingredients of each formulation were melted and mixed at 90° C. for 12 hours in a sealed glass container. The material was then allowed to cool down to 58° C. or 80° C. (at which temperature the material is still molten) and equilibrated for 2 hours at that temperature before the molding experiment.

Molding was conducted using the mold apparatus described earlier. The pre-assembled mold was kept at room temperature, −5° C., or −32° C. (this latter temperature achieved using an isopropyl alcohol/dry ice mixture) for 1 or more hours until the temperature reached equilibrium before each molding experiment. The molten formulation was dispensed into the mold filling up three separate mold cavities. Except for the −32° C. samples, the material in the mold was allowed to cool while the mold was kept at room temperature. During the cooling of the −32° C. experiment, the mold was maintained at −32° C. As it is hazardous to conduct experiments in liquid nitrogen, the −32° C. set of samples were an attempt to come very close to a simulation of the molding conditions described in the prior art without incurring injury.

In each molding cycle, the materials were substantially fully set after 10 minutes. The mold was kept at room temperature for another 2 hours until the mold temperature equilibrated to room temperature. De-molding was carried out using the matching de-molding pin set. The demolded parts were evaluated based on their appearance, touch, and the malleability of the molded materials.

The molding process produced cylindrical rods about 8 mm×20 mm in dimension. The three molded parts generated from each formulation under the same molding condition exhibited consistent material properties. Molded cylindrical sticks exhibited a cylindrical central void in the upper portion of the molded parts due to cooling and shrinking. This however, did not affect the overall material evaluation; void formation due to shrinking can be minimized or prevented by molding under pressure or in a closed mold, if desired.

The mean properties of the molded PLURONIC® polymers are listed in Tables 1, 2, and 3 below. These include both descriptive data and a semi-quantitative ranking for each property of interest. The properties of samples made using the 80:20 ratio of PLURONIC® P85 and F88 combination molded with the mold at room temperature were used as a baseline reference point. The initial property evaluation includes the inspection of the material appearance, the number of cracks in each of the molded sticks, and the stickiness of the material when touched by instrument and gloved hand. The evaluation of the working properties of the materials includes the hardness, malleability, adhesion and cohesion.

The data (see Tables 1, 2, and 3) show that the physical properties of the molded materials vary significantly with both the copolymer ratio and the molding conditions. In general, increasing the concentrations of the solid, high melting PLURONIC® F88 component tends to increase the hardness and brittleness, and reduce the plasticity of the molded material. However, within a given formulation ratio, it was unexpectedly found that the properties of the molded parts also vary significantly depending upon the mold temperature. Molten polymeric alloy material cooled in a mold set at room temperature tends to generate softer and more malleable materials.

Across all three copolymer ratios, there is a significant difference between the polymer alloys molded quickly cooled at temperatures below 0° C. and those molded at room temperature. This difference is reflected in the number of cracks, the material hardness, stickiness and the malleability of such materials. For example, all materials molded at −32° C. exhibit two to three crack lines. The cracks were generated either during the material cooling and/or the de-molding process. Once at room temperature, these materials are relatively rigid and hard compared with the same formulation cooled more slowly and under milder conditions. Materials molded in a −5° C. mold showed fewer average crack lines, while those molded at 27° C. have no crack lines at all. In addition, the molten copolymer alloy sticks molded at a 58° C. starting temperature (rather than a beginning molding temperature of 80° C.) show fewer crack lines than those molded from a starting temperature 80° C.

Crack formation is an indication that the molded material is brittle, does not coalesce well, and/or is rigid. The cracks form perpendicularly to the long axis of the cylindrical molded parts. The average number of cracks among the formulations tested ranging from 3 to 0. For the molding experiment cooled using a −32° C. mold maintained at −32° C., all the molded cylindrical parts exhibit 2-3 crack lines when the molded material was brought to room temperature and ejected with the demolding pin set, irrespective of the formulation ratios. The number of crack lines observed in all molded parts is consistent within each molding cycle.

These quickly-cooled molded mixed copolymer materials are substantially different from alloys made using the same materials, but cooled more slowly: in general, the faster cooled alloys are not optimally malleable for use as a bone hemostatic wax. More importantly, the conditions employed are not suitable for practicable mass production. Based on these results, materials molded in a liquid nitrogen cooling medium will be significantly and substantially more rigid and thus less optimal for use as a bone hemostat when compared with copolymer materials made exactly the same way, but prepared using slower or more mild cooling conditions.

In this experiment the most striking difference between alloys made and blended identically, but cooled differently was observed on compositions of a 90:10 ratio of PLURONIC® P85 and F88, the preferred embodiment of the prior art, under different molding/cooling conditions. All three alloy "sticks" molded and cooled in a −32° C. mold, then brought back to room temperature were relatively rigid and non-sticky and each exhibited two to three crack lines. Each "stick" required kneading by hand to soften the material before it became malleable and sticky.

By contrast, the compositions made of the blended 90:10 ratio of PLURONIC® P85 and F88 molded in a mold held at 27° C. were so soft and sticky that they all deformed (without cracking) during demolding. They were very soft and easily deformed upon touch, exhibiting a consistency similar to ointment or reverse-phase aqueous gel prepared from PLURONIC® F127 material. While such alloys might require a stiffening agent for use as bone haemostatic agent for lack of cohesiveness, they are clearly different from the more rapidly and drastically cooled, but otherwise identical alloy. Moreover, alloy material having these softer, more malleable characteristics is suitable for other medical applications, such as for use as a hemostatic agent or wound dressing to control soft tissue bleeding. The slowly cooled alloy material can be easily spread on soft tissues and remain in place.

Furthermore, unlike beeswax, soluble bone wax, or the other, harder, molded alloy materials prepared in the present Example, these softer alloy materials left no unsightly solid opaque wax residue on tissue surfaces after application. Such properties are particularly useful as a hemostatic agent and wound dressing for superficial wounds, including burn wounds, facial wounds, and wounds created after laser skin resurfacing of the facial tissues, and for use in health and beauty applications, such as a cream or ointment.

The compositions blended at a 80:20 weight ratio of P85 and F88 and subsequently cooled in a room temperature mold at room temperature from 58° C. and 80° C. molten materials produced a material with better malleability compared with other compositions prepared in this series of experiments.

Results are shown in the following Tables 1-3.

TABLE 1

Properties of 90:10 ratio of PLURONIC ® P85 and F88 Alloy

| P85:F88 90:10 | Molten Temp °C. | Mold Temp °C. | General Properties | | Working Properties | | Adhesion/cohesion |
|---|---|---|---|---|---|---|---|
| | | | Ave. # Cracks | Stickiness | Hardness | Malleability | |
| 1 | 80 | −32 | 3 | 2 | 3.5 | 4 | 1/3 |
| 2 | 80 | −5 | 0.7 | 2 | 3.5 | 4 | 2/3 |
| 3 | 80 | 27 | 0 | 5 | 1 | 2 | 5/1 |
| 4 | 58 | −32 | 2 | 2 | 3 | 3 | 1/3 |
| 5 | 58 | −5 | 0 | 2 | 2 | 3 | 2/3 |
| 6 | 58 | 27 | 0 | 5 | 1 | 1 | 5/1 |

TABLE 2

Properties of 80:20 ratio of PLURONIC ® P85 and F88 Alloy

| P85:F88 80:20 | Molten Temp °C. | Mold Temp °C. | General | | Working Properties | | Adhesion/cohesion |
|---|---|---|---|---|---|---|---|
| | | | Ave. # Cracks | Stickiness | Hardness | Malleability | |
| 1 | 80 | −32 | 3 | 2 | 4 | 5 | 1/2 |
| 2 | 80 | −5 | 3 | 2 | 4 | 5 | 1/3 |
| 3 | 80 | 27 | 0 | 3 | 3 | 4 | 4/3 |
| 4 | 58 | −32 | 3 | 2 | 4 | 5 | 2/2 |
| 5 | 58 | −5 | 1 | 2 | 4 | 4 | 3/3 |
| 6 | 58 | 27 | 0 | 3 | 3 | 3 | 4/3 |

TABLE 3

Properties of 70:30 ratio of PLURONIC ® P85 and F88 Alloy

| P85:F88 70:30 | Molten Temp °C. | Mold Temp °C. | General | | Working Properties | | Adhesion/cohesion |
|---|---|---|---|---|---|---|---|
| | | | Ave. # Cracks | Stickiness | Hardness | Malleability | |
| 1 | 80 | −32 | 3 | 1 | 5 | 6 | 1/5 |
| 2 | 80 | −5 | 3 | 1 | 4 | 5 | 2/4 |
| 3 | 80 | 27 | 0 | 1 | 4 | 4 | 4/3 |
| 4 | 58 | −32 | 3 | 1 | 4 | 5 | 1/5 |
| 5 | 58 | −5 | 2 | 1 | 4 | 5 | 2/3 |
| 6 | 58 | 27 | 0 | 1 | 4 | 4 | 5/3 |

The numerical scale used in these and the following Examples as follows:

Stickiness is ranked from 1 to 5 with increasing stickiness, including (1) very non-sticky, (2) non-sticky, (3) medium, (4) sticky, and (5) very sticky.

Material hardness is graded from 1 to 5 with increasing material hardness, including (1) very soft, deformed upon touch, (2) soft, (3) medium, (4) hard, (5) very hard.

Malleability is the capability of the material to be reshaped by hand and reflects the combined plasticity and the physical properties of the material. It is rated from 1 to 6, as follows: (1) deformed with minimal force, (2) soft, easily malleable (3) medium, malleable (4) hard, malleable, (5) breaks, tears, crumbles, (6) rock hard, not malleable.

The adhesion/cohesion factor reveals the material's strength in each of adhesion and cohesiveness when the material is manipulated or kneaded by a gloved hand. Each is ranked from 1 to 5, as follows: (1) very low, (2) low, (3) medium, (4) high, and (5) very high.

EXAMPLE 3

Cooling Profiles of 90:10 Ratio of PLURONIC® P85 and F88 Blend

The cooling profiles of the molten PLURONIC® P85 and F88 blended at a 90:10 ratio, when molded under different cooling conditions were studied to investigate the cause of the significant differences in the structural properties of the otherwise identical alloy materials, as exhibited by the molded articles.

PLURONIC® P85 and F88, blended at a 90:10 ratio, was prepared as described before, and molded as also described above. After the molten material was dispensed into a mold cavity, a thermocouple was inserted into the center of the filled mold cavity. The temperature of the material was recorded every 15 seconds. The lapsed time between dispensing of the molten material and the first temperature reading is about 10-12 seconds.

Three mold temperature: room temperature (27° C.), −5° C., and −32° C. was studied. In the 27° C. and −32° C. studies, the mold was maintained at a constant temperature. For the −5° C. study, the mold was initially cooled to −5°, and was then kept at ambient (room) temperature when the molten material was dispensed into the mold and after the mold was filled. The results are plotted in FIG. 1.

In the cold molds, −32° C. and −5° C., the cooling profiles of the blended molten materials exhibit a relatively linear cooling profile for the first two minutes (until the temperature reaches equilibrium). However, in the 27° C. mold, an unexpected exothermic event occurs at about 1.75 minutes after the mold is filled and cooling started. This exothermic event temporary raised the material temperature and significantly extended the cooling profile. It was initially unclear what caused this exothermic event, and whether there was any relationship between the exothermic event and the unexpected properties of PLURONIC® block copolymers cooled in a room temperature mold.

Figure 2:
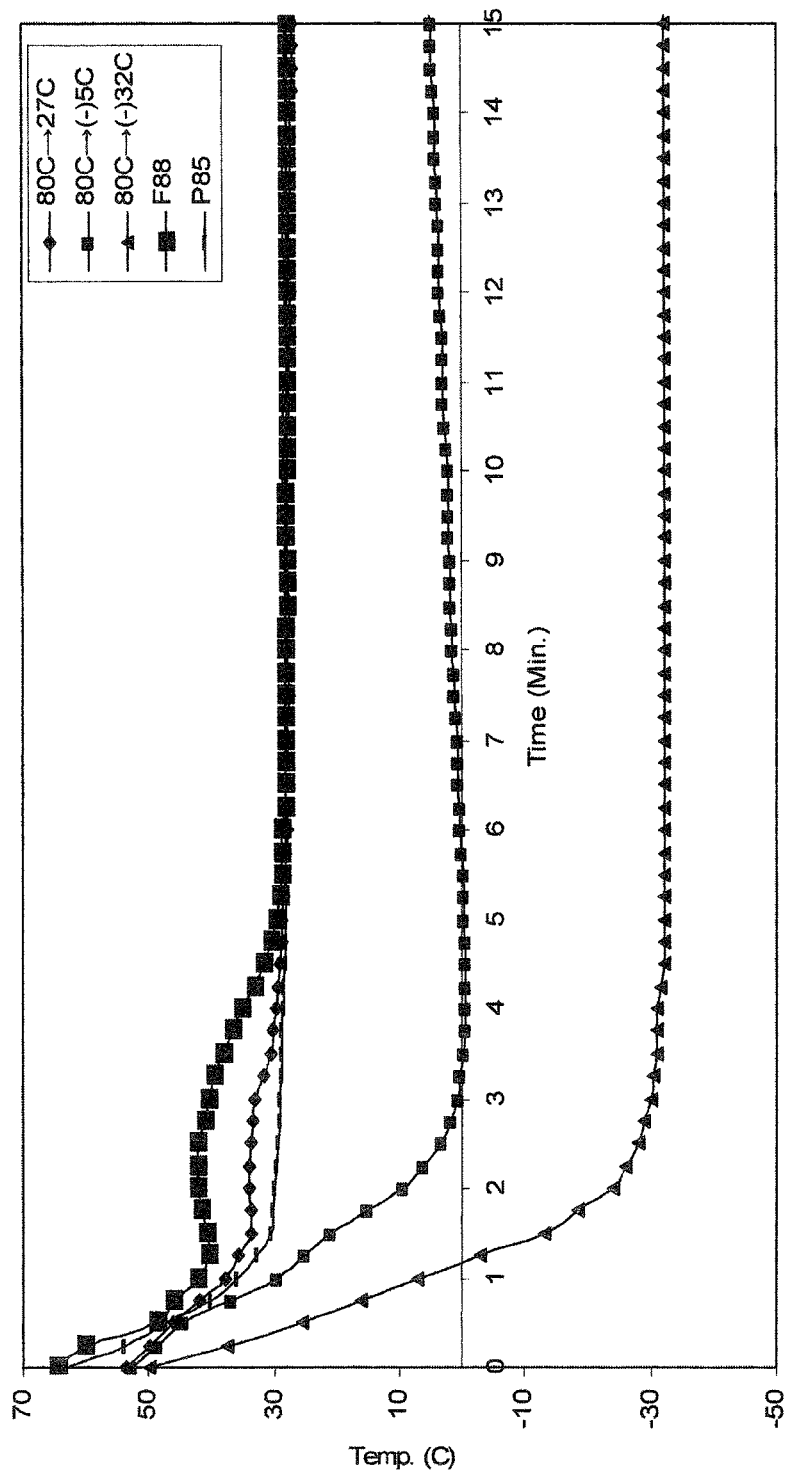
FIG. 2 is a plot of temperature versus time for cooling profiles of PLURONIC® P85 and F88 blend, and each of P85 and F88 alone, respectively.

To elucidate the cause of this unknown exothermic event, the 27° C. cooling profiles of the component PLURONIC® block copolymers F88 and P85 were individually studied, respectively, using the same procedures as described above. These cooling profiles were then superimposed with those previously obtained from the blended PLURONIC® P85 and F88 formulations, as shown in FIG. 2.

The superimposed cooling profiles show that the main contribution of the unexpected exothermic event is from the exotherm of the PLURONIC® F88 block copolymer; little, if any, exothermic components of the cooling profile for the P85 component are detected. The cooling profile of the blended 90:10 ratio of PLURONIC® P85 and F88 is clearly a composite of the respective cooling profile of the PLURONIC® P85 and F88 block copolymers.

EXAMPLE 4

Cooling Rates of 90:10 Ratio of PLURONIC® P85 and F88 Blend

The cooling rate of the molten material can be estimated from the slope of the cooling profiles. The initial, first minute, cooling rates for blended 90:10 PLURONIC® P85 and F88 alloys were calculated from the slopes of the cooling profiles, and were found to be −15° C./min, −23° C./min, and −42° C./min, respectively for 27° C., −5° C. and −32° C. mold. This indicates that a cooling rate of about −15° C./min or less will result in microcrystalline formation in such a PLURONIC® alloy. While not directly measured, it is estimated based on the results from this study and the temperature of the liquid nitrogen (−196° C.), that alloy cooled in the manner carried out in this experiment from 80° C. in liquid nitrogen should have a cooling rate of about −120° C./min.

EXAMPLE 5

PEO Molecular Weight, Crystallinity Content and Hydrophore Content

The average molecular mass of the PEO block and the amount of PEO in PEO-containing block copolymers, such as PLURONIC® block copolymers, are available from the vendor or are known from the synthesis of the material. For example, the information of some PLURONIC® block copolymers, including P85, F88, P123, F127, L35 and F38 obtained from BASF, the PLURONIC® supplier, are given in Table 4 below. Based on this information and the results obtained from the molding/cooling study, the approximate average molecular mass of the PEO that forms microcrystals detectable in these studies, the hydrophore content, and the maximum crystallinity content that may be attained from the cooling process can be estimated and/or calculated.

TABLE 4

Melting Point and Molecular Weight of PLURONIC ® Block Copolymers

| PLURONIC ® | Melting Point (° C.) | M.W. (g/mol) | PEO Block M.W. (g/mol) | % Weight PEO |
|---|---|---|---|---|
| F88 | 54 | 11400 | 9120 | 80 |
| P85 | 34 | 4600 | 2300 | 50 |
| F127 | 56 | 12600 | 8820 | 70 |
| P123 | 31 | 5750 | 1725 | 30 |
| F38 | 48 | 4700 | 3760 | 80 |
| L35 | 7 | 1900 | 950 | 50 |

For example, one may add the products of the molecular weights of the hydrophobic moiety and the percent of each co-polymer to reach an estimate of the hydrophore content. Thus, a 90:10 ratio of PLURONIC® P85 and F88 alloy has a hydrophobic block (hydrophore) content of ((0.1×0.2)+(0.9×0.5))=0.47 or 47%. This copolymer mixture may therefore attain a maximum crystallinity content of ((0.1×0.8)+(0.9×0.5))=0.53 or 53%, if all the PEO blocks form microcrystallines. If the cooling profiles are adjusted to allow predominately the PEO blocks of the F88 to crystallize as it has a higher melting point than the P85, then the maximum crystallinity content will be (0.1×0.8)=0.08 or 8%.

Similarly, a 50:50 mixture of PLURONIC® P123 and F127 has a hydrophore content of 50%, and may contain a maximum crystallinity of 50%. It also becomes apparent from the above analysis that certain PEO block lengths may have a greater propensity to crystallize than others under the conditions set forth above.

EXAMPLE 6

Preparation of PLURONIC® Alloys of P123 and F127 Blend

Two molten material temperatures (80° C. and 62° C.), two mold temperatures (room temperature 25° C. and −5° C.), and two different formulation ratios, 50:50 and 60:40 of PLURONIC® P123 and F127 materials, were used in this study. The ingredients of each formulation were melted and mixed at 90° C. for 12 hours in a sealed glass container. The molten temperature of the material was then allowed to cool down to 62° C. or 80° C., respectively, and equilibrated for 2 hours at that temperature before the molding experiment. Molding was conducted using the mold set up described In Example 1 above. The pre-assembled mold was kept at room temperature 25° C., or −5° C. before each molding experiment. Each molten alloy formulation was dispensed and used to fill three mold cavities spaced evenly apart. The alloy in the mold was allowed to cool while the mold was kept at room temperature. In each molding cycle, the materials were fully set after 10 minutes. De-molding was carried out an hour later using the matching de-molding pin set. The molded PLURONIC® alloys were evaluated based on their appearance and the malleability of the molded materials. All of the molded PLURONIC® alloys were translucent. The average properties of the molded polymer alloy are listed in Tables 5 and 6 below. Among other property differences, parts cooled in sub-ambient molds showed cracks, while those molded/cooled in a 25° C. (room temperature) mold did not show cracks.

In a separate set of experiments, PLURONIC® P123 and F127 alloys containing 9 wt % F127, and 18 wt % F127, respectively, were prepared as described above. The consistency of the material was evaluated and listed in Table 7. PLURONIC® P123 and F127 alloys containing 9% and 18% F127 content, respectively, were found to exhibit a consistency similar to that of the F127 reverse phase aqueous gel at room temperature. The alloy with 18% F127 content was significantly more viscous than the one with 9% F127 content.

TABLE 5

Properties of 50:50 Ratio of Molded PLURONIC ® P123 and F127 Alloy

| P123: F127 50:50 | Molten Temp ° C. | Mold Temp ° C. | Working Properties | | | | |
|---|---|---|---|---|---|---|---|
| | | | General | | Hardness | Malleability | Adhesion/ cohesion |
| | | | Ave. # Cracks | Stickiness | | | |
| 1 | 80 | −5 | 2.7 | 1 | 5 | 6 | 1/1 |
| 2 | 80 | 25 | 0 | 1.5 | 4 | 5.6 | 2/2 |
| 3 | 62 | 25 | 0 | 2 | 4 | 5.6 | 2/3 |

TABLE 6

Properties of 60:40 Ratio of Molded PLURONIC®
P123 and F127 Alloy

| P123: F127 50:50 | Molten Temp °C. | Mold Temp °C. | Working Properties | | | | |
|---|---|---|---|---|---|---|---|
| | | | General | | | | Adhesion/ |
| | | | Ave. # Cracks | Stickiness | Hardness | Malleability | cohesion |
| 1 | 80 | −5 | 1 | 1 | 5 | 5.6 | 1/1 |
| 2 | 80 | 25 | 0 | 2 | 4 | 4 | 2.5/3 |
| 3 | 62 | 25 | 0 | 2 | 4 | 4 | 2.5/3 |

TABLE 7

Consistency of PLURONIC® P123 and F127 Alloy

| Exp. ID | P123 (g) | F127 (g) | Wt % F127 | Consistency |
|---|---|---|---|---|
| 111410-1 | 20.65 | 2.05 | 9 | Gel |
| 111410-2 | 1.83 | 0.41 | 18 | Gel |

EXAMPLE 7

Cooling Profiles of 50:50 Ratio of PLURONIC®
P123 and F127 Blend

Figure 3:
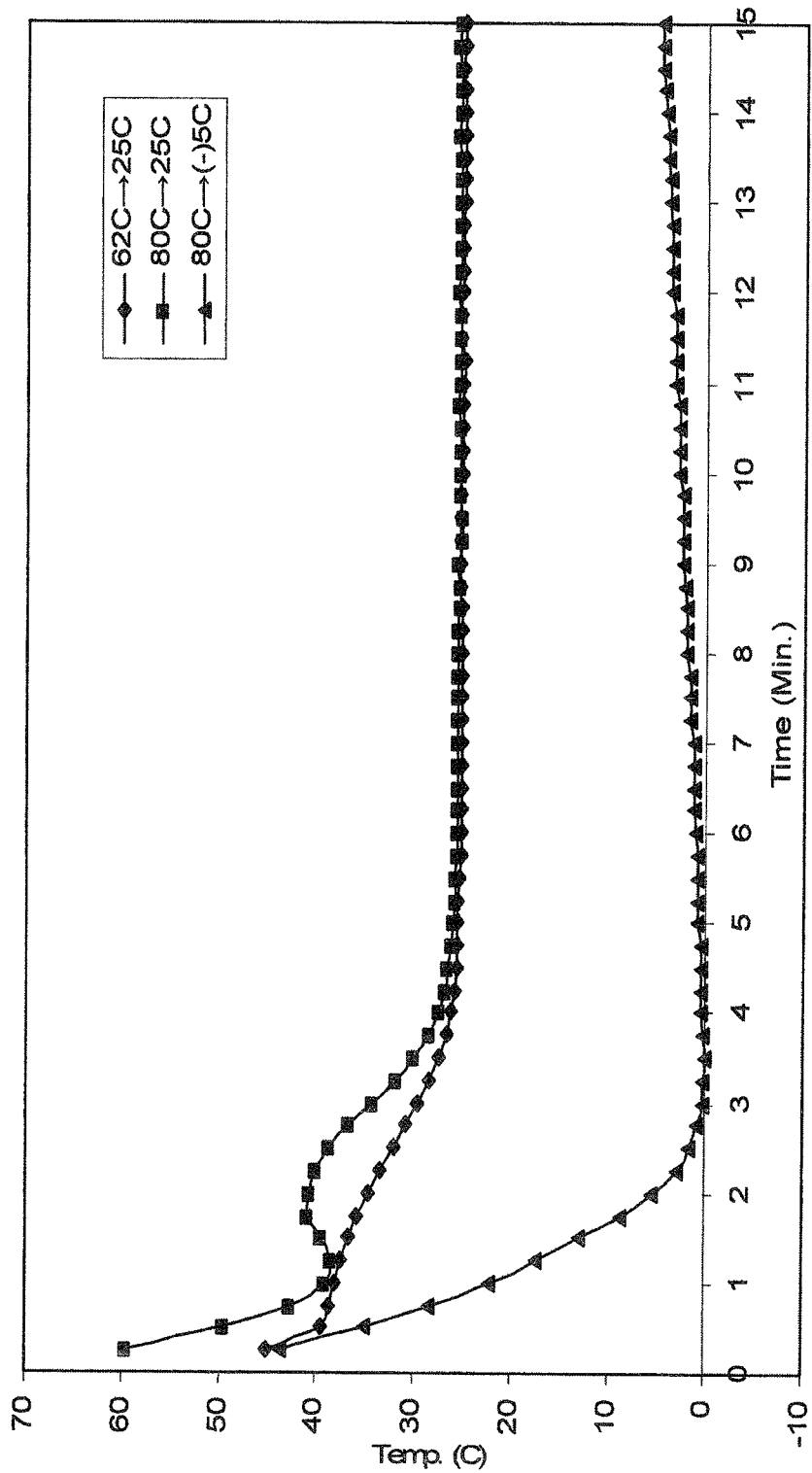
FIG. 3 is a plot of cooling profiles of 50:50 ratio of PLURONIC® P123 AND F127 blend cooled according to different methods.

The cooling profiles of molten blended alloys comprising a 50:50 weight ratio of PLURONIC® P123 and F127 Blend were studied as described before. FIG. 3 shows three material cooling profiles of the 50:50 P123 and F127 alloy blend. Initial cooling of the molten blend material from 80° C. to −5° C. exhibited a near linear cooling rate, similar to that seen in the cooling of P85/F88 formulation. The slower cooling profiles (80° C. to 25° C. and 62° C. to 25° C.) reveal the exothermic effect (within the first 2 or 3 minutes) of the heat of crystallization and transition of the material. The alloy cooling profile was significantly flattened by lowering the molten material temperature from 80° C. to 62° C.

Figure 4:
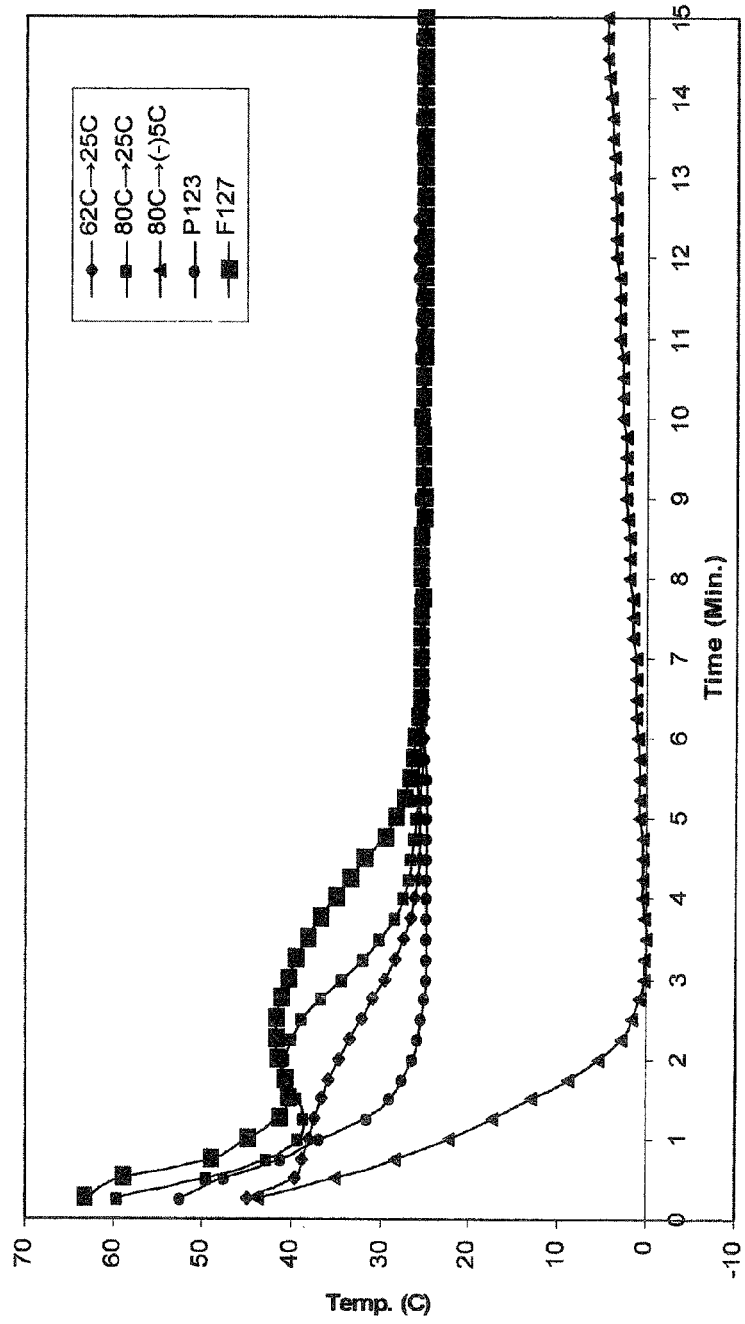
FIG. 4 is a plot of cooling profiles of 50:50 ratio of PLURONIC® P123 and F127 Blend, and each of P123 and F127 alone, respectively.

The individual cooling profiles of P123 and F127, respectively, from 80° C. to 25° C. were also evaluated and overlaid together with those of the P123/F127 blend in FIG. 4. It was again found that under this cooling condition, the P123 component which contains a shorter segment of polyethylene oxide did not show signs of exothermic crystallization. In this case, the molecular mass of PPO block in both P123 and F127 is 3600 g/mole, while the molecular mass of the PEO blocks in P123 and F127 are 2150 g/mole and 9,000 g/mole, respectively. Since the formation of polymer microcrystals, such as the shape, size and amount of spherulite and/or lamellae, is affected by the cooling profile one can optimize the material properties by controlling the cooling profile of the molten material.

As above, this study confirms that under the same conditions, the cooling rate is dictated in part by the temperature differential of the molten material and the mold. At a slow cooling rate when phase transition is given time to occur, the cooling rate is a composite of the exothermic phase transition process and the linear temperature differential of the mold and the molten material. The study also confirms that low molecular weight PEO does not undergo substantial phase transition while the high molecular weight PEO does under such molding/cooling conditions. In addition, this experiment shows that the composite cooling profile can be significantly affected by the starting molten temperature of the polymeric alloy.

EXAMPLE 8

Cytotoxicity Test And Hydrophobic Content

The following polymer alloys were prepared for cytotoxicity testing as test materials. Cylindrical alloy sticks were made of a 90:10 weight ratio of PLURONIC® P85 and F88. The alloys were prepared by cooling the molten mixture (held at 80° C.) in a mold pre-chilled to −30° C. mold, similar to existing methods of preparation. Additionally, cylindrical alloy sticks of a 60:40 weight ratio of PLURONIC® P123 and F127 were prepared by cooling a 80° C. molten mixture in a 25° C. mold. Also, for comparison purposes Ostene® bone hemostat, a composition made from a mixture of random and non-random copolymers as described in U.S. Pat. No. 7,55, 913 (obtained from Ceremed, Inc.) was procured for testing.

The hydrophobic content of each alloy was calculated based on the percentage of PPO blocks present in each composition. Hydrophilic random copolymers of PEO-PPO contain no PPO blocks, but rather have an random, distribution of PEO and PPO monomeric units.

The cytotoxicity test was performed according to the USP/AAMI/ISO 10993-5 standard. Briefly, six-well cell culture plates were seeded with a verified quantity of industry standard L-929 cells (ATCC CCL-1) and incubated at 37° C. (±1° C.) with 1% $CO_2$ until approximately 80% confluent. The agar overlay consisted of an equal mixture of 2× agar (1.0%) and 2× Eagle's minimum essential medium (MEM)+10% bovine calf serum. The test materials were placed directly on the solidified agar, no less than 100 mg per well. After addition of the test materials, the cell culture plates were incubated as described above for 24-26 hours. A triplicate test was performed on each sample. Positive and negative reference controls were included with each assay.

Following incubation, cells were evaluated microscopically. The toxicity of the material was rated from 0 to 4 according to the International Organization Of Standardization (ISO) 10993-5 standard criteria. The average score of triplicate plates given the same test material was used to judge the cytotoxicity of each test material. A rating of more than 2 is considered cytotoxic, and would fail the cytotoxicity test. The results are listed in Table 8 below.

TABLE 8

Cytotoxicity And Hydrophobic Content

| Material | Hydrophobic Content (%) | Cytotoxicity |
|---|---|---|
| 90:10 ratio P85:F88; flash-cooled | 47 | Fail |
| 60:40 ratio P123:F127; slow cooled | 54 | Pass |
| Ostene® | 10~15 | Pass |

EXAMPLE 9

Molding of 60:40 Ratio of PLURONIC® P123 and
F127 Blend

A composition was made comprising a 60:40 weight ratio of PLURONIC® P123 and F127, melt-blended and molded as described earlier. The pre-assembled mold was kept either at room temperature (25° C.), or 80° C. for 1 or more hours until the temperature reached equilibrium before each molding experiment. For each temperature, the molten mixture was dispensed into and permitted to fill all 25 mold cavities. In each case, the alloy in the mold was allowed to cool while the mold was kept at room temperature. Demolding was conducted using the matching de-molding pin set 4 hours later either by hand, or by the use of a mechanical press if required.

Demolded alloys were evaluated based on their appearance, touch, and the malleability of the molded materials. Each molding cycle produced 25 polymer alloys with consistent properties within each set. All molded parts were successfully ejected and showed no signs of cracking. The PLURONIC® alloy parts produced from the 80° C. mold exhibited a shining and white opaque color, requiring minimal force to demold by hand pressure. In contrast, the translucent/opaque parts produced in the 25° C. mold lacked luster and stuck firmly to the mold, requiring the use of a mechanical press to eject the parts. This material was, however, significantly more malleable when compared with the material molded in an 80° C. mold and then cooled.

The test results of the molded materials are listed in Table 9 below. As shown in Table 9:

(A) Microcrystalline-containing PLURONIC® block copolymers alloys having the highest average molecular weight commercially available can be reproducibly mass-produced consistently according to the present invention without molding defects, and B) By adjusting the cooling rate of the same molten PLURONIC® blend (e.g., by varying the temperature of the mold at the outset of cooling), one can produce polymer alloys with diverse mechanical and surface properties.

C) As the crystallinity content increases, the contribution of the crystallized polymer component to the bulk polymer alloy's property decreases, while at the same time, the property contribution of the non-crystallizable polymer component is enhanced. For example, in this case, as more hydrophilic PEO packed into tight crystalline structures which are dispersed within and surrounded by hydrophobic PPO polymer segments, the polymer alloy becomes more hydrophobic, and does not stick as much to the mold surface compared with the alloy with less crystalline content. Thus, the present invention also provides a method to adjust both the mechanical and surface properties of the polymer alloy by controlling the crystallinity content of the alloy composition.

TABLE 9

Relative Properties of 60:40 Ratio of PLURONIC ® P123 and F127 Alloy

| Material P123: F127 | Mold Temp | Demolding by | Appearance | Feel | Malleability |
|---|---|---|---|---|---|
| 60:40 ratio | 25° C. | Hand | Translucent Lack-luster | Nonslick | 4 |
| 60:40 ratio | 80° C. | Press | White/opaque Luster | Slick | 5.6 |

EXAMPLE 10

Dissolution Study of Ostene and 60:40 Blend of PLURONIC®P123 and F127

Materials:
1. Ostene® water soluble bone hemostasis material from Ceremed®.
2. 60:40 ratio of PLURONIC® P123 and F127 alloy molded/cooled in a 25° C. mold.
3. 60:40 ratio of PLURONIC® P123 and F127 alloy molded/cooled in a 80° C. mold.

Procedures:
Three approximately 3 mm×6 mm disks were punched out from each of the materials. Each of the disks were weighed and then placed in the center of a 9 cm diameter Petri dish. 40 millimeters of distilled water was added to each Petri dish to cover the disks.

The dissolution pattern of each disk was monitored and the time required for the disk to dissolve completely at 21° C. was recorded.

Results:
Table 10 lists the dissolution rate of Ostene® and the 60:40 blends of P123 and F127. The dissolution rate of the 60:40 blend of P123 and F127 prepared according to the present invention is 187% (for the alloy cooled in a 25° C. mold) and 203% (for the alloy cooled in a 80° C. mold) slower than that of Ostene®. There was no appreciable swelling during the dissolution of either material. The exterior of the disk gradually dissolved over time and the size of the disk continued to shrink until it completely dissolved.

During dissolution, the Ostene® disk remained opaque, while its size continued to reduce until complete dissolution. On the other hand, the dissolution of the 60:40 blends of P123 and F127 followed a distinctly different pattern. Within minutes after immersion in water, a distinct ring of aqueous gel formed around the opaque disk. As the disk continued to reduce in size during dissolution, the distinct aqueous gel ring remained around the opaque disk until the disk was completely dissolved.

Figure 5:
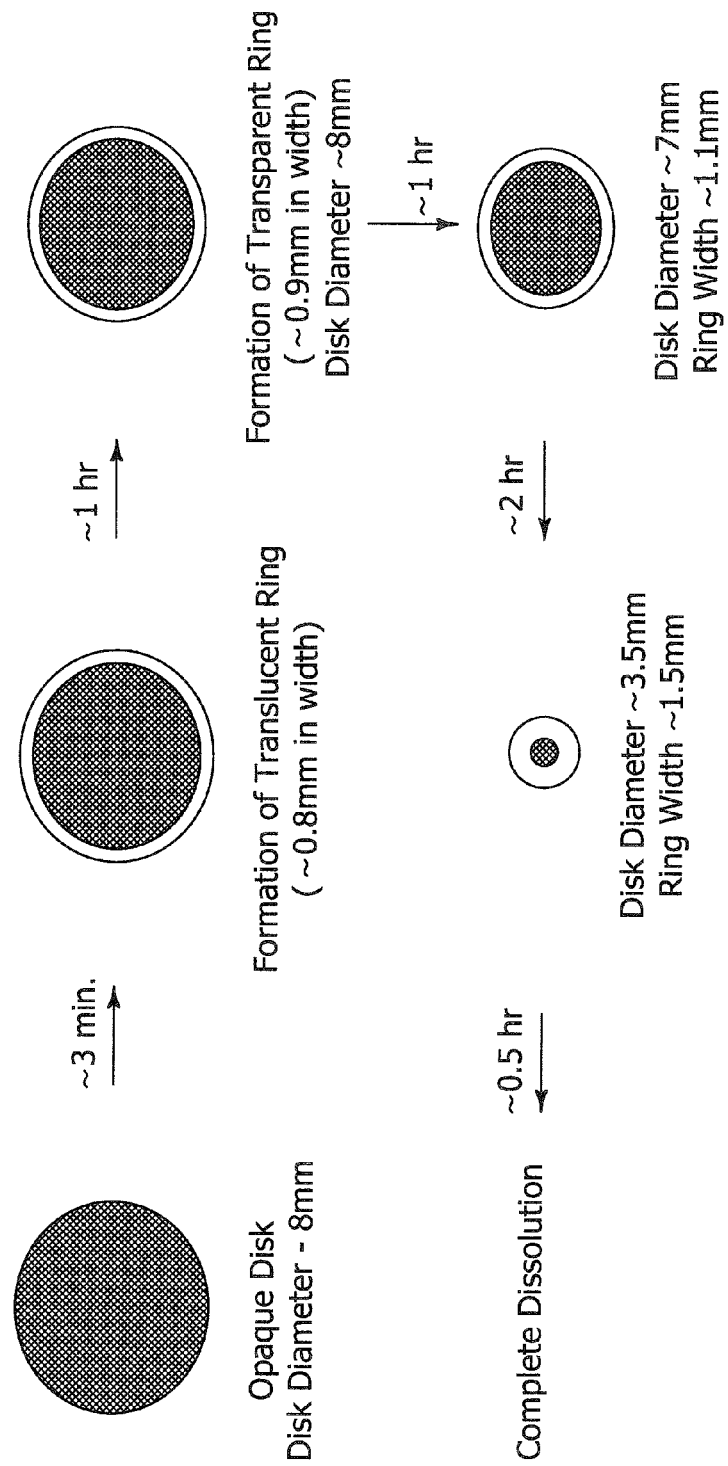
FIG. 5 is a diagram illustrating the dissolution pattern of an alloy comprising a 60:40 ratio of PLURONIC® P123 and F127.

The dissolution pattern of the 60:40 blends P123 and F127 (cooled in a 25° C. mold) was carefully monitored in a separate study using a 3 mm×8 mm disk prepared as described earlier. The dissolution pattern of the disk is illustrated in FIG. 5. The dissolution of the material was found to follow a three-step process: (1) diffusion of water into the opaque material, (2) dissolution of the exterior of the microcrystalline-containing material to form a clear gel, and (3) dissolution of the clear gel. The process continues from the exterior of the surface and progresses until the material completely dissolves. The exterior of the material forms a distinct ring of clear gel in 3 minutes after the material is immersed in water. The disk material shrinks over time, but the width of the ring remains relatively constant (~0.8-1.5 mm) throughout the course of dissolution (approximately 210 minutes).

This indicates that the dissolution of the material is governed by two key parameters (A) the diffusion of water into the material and the dissolution of the solid material to form a clear gel (rate R1), and (B) the dissolution of the clear gel (rate R2). If R1 is significantly greater than R2, the ring width would have rapidly increased over time. On the other hand, if R2 is significantly greater than R1, the ring width would have significantly decreased over time. Since the ring width does not vary significantly during dissolution, R1 and R2 are likely in the same order of magnitude and remain relatively constant throughout the course of the dissolution. No appreciable material swelling was observed during dissolution. The material maintains its shape while continuing to shrink over time. Overall, this indicates that the material steadily dissolves at a relatively constant rate until the bulk of the material dissolves. Materials prepared according to the prior art lack such advantageous properties and exhibit a substantially faster dissolution rate.

TABLE 10

Dissolution data of Ostene and 60:40 blend of P123 & F127

| Material | Material wt (gram) | Dissolution duration (min) | Rate (min/gram) |
|---|---|---|---|
| Ostene | 0.09 | 84 | 933 |
| W2190308 | 0.10 | 91 | 910 |
|  | 0.09 | 95 | 1055 |
|  |  |  | Ave 966 |
| 60:40 blend P123 & F127 25° C. mold | 0.10 | 163 | 1630 |
|  | 0.10 | 176 | 1760 |
|  | 0.10 | 203 | 2030 |
|  |  |  | Ave 1806 |
| 60:40 blend P123 & F127 80° C. mold | 0.10 | 179 | 1790 |
|  | 0.10 | 210 | 2100 |
|  | 0.09 | 183 | 2020 |
|  |  |  | Ave 1970 |

EXAMPLE 11

Preparation of Sudan IV-Containing PLURONIC® Alloys

Sudan IV (certified, Sigma) was chosen as a surrogate for hydrophobic pharmaceutical agents. Sudan IV is a highly hydrophobic and highly conjugated dye used as a lipid stain. This dye is almost completely insoluble in water and represents a challenging drug model for dispersion study.
Preparation of PLURONIC® Alloys
  1. 60:40 blend of PLURONIC® P123 and F127 was prepared as described above.
  2. 50:50 blend of PLURONIC® F127 and PLURACOL® V10 was prepared as disclosed in Example 7 of U.S. Pat. No. 7,553,913.
Preparation of Sudan IV Containing PLURONIC® Alloys
  0.07 gram of Sudan IV was added into 13.87 gram of 60:40 blend of PLURONIC® P123 and F127. The mixture was melted and mixed at 90° C. for 10 hours. The molten dark red color mixture was poured into a 3 mm×11 mm×50 mm rectangular mold and allowed to cool to room temperature (24° C.) (Composition A). Similarly, a mixture of 0.06 gram of Sudan IV in 12.07 gram of 50:50 blend of PLURONIC® F127 and PLURACOL® V10 was prepared and molded (Composition B).
  Sudan IV dispersed and dissolved much more rapidly into the blend of PLURONIC® P123 and F127 than into the PLURONIC® F127 and PLURACOL® V10 blend. Within an hour, the bulk of Sudan IV had dissolved into the PLURONIC® P123 and F127 blend and formed a dark red homogeneous solution. In contrast, only about 50% of Sudan IV dispersed locally into the PLURONIC® F127 and PLURACOL® V10 blend and formed clumpy dark red clouds within the molten blend of PLURONIC® F127 and PLURACOL® alloy. Agitation speeds up the dispersion of Sudan IV into the PLURONIC® alloys. After demolding, both Sudan IV-containing PLURONIC® alloys were tested and found malleable.

EXAMPLE 12

Dissolution Study of Sudan IV-Containing PLURONIC® Alloys

Dissolution of Compositions A and B prepared in Example 11 was conducted as described in Example 10 at 23.8° C. The rates of material dissolution were calculated and listed in the Table 11 below. Composition A gradually dissolved and formed homogeneous red color solution radiating from the disk. Composition B gradually dissolved, but formed clumpy, scattered clusters of dye-containing PLURONIC® materials in a mostly clear solution. Similar to the dissolution of a non dye-containing disk made of PLURONIC® Alloy, there was a distinct, transparent ring surrounding the dark red disk of dye-containing Composition A. In contrast, the ring surrounding Composition B was opaque and obscure with some clumpy dye-containing PLURONIC® materials directly attached to the disk of Composition B. These demonstrate that formation of Sudan IV-containing micelles took place within the distinct, transparent ring of Composition A and then diffused into the solution as mixed micelles. On the contrary, Composition B was not capable of providing such a well defined transition zone to form stable micelles. As a result, the content of Composition B disintegrated into the surrounding solution upon erosion of the disk, and Sudan IV subsequently precipitated in the solution. This study demonstrates that PLURONIC® alloys prepared according to the present invention performs significantly better for the delivery of hydrophobic agents than those prepared according to the prior art.

TABLE 11

Dissolution Rates of Sudan IV-containing PLURONIC ® Alloys

| Material composition | Material wt (gram) | Dissolution duration (min) | Rate (min/gram) |
|---|---|---|---|
| A | 0.09 | 216 | 2400 |
|  | 0.09 | 201 | 2233 |
|  | 0.09 | 218 | 2422 |
| Ave | 0.09 | 211 | 2351 |
| B | 0.08 | 167 | 2088 |
|  | 0.09 | 158 | 1756 |
|  | 0.09 | 180 | 2000 |
| Ave | 0.09 | 168 | 1948 |

EXAMPLE 13

Stability of Sudan IV-Containing Mixed Micelles

Approximately 0.18 gram of Compositions A and B, prepared as in Example 11, were separately dissolved in 6 ml of distilled water for 6 hours with agitation. The solution was filtered through a 0.22 um, sterile polyethersulfone (PES) filter (Life Science Products, Inc.) into a clear glass vial. The filtered Composition A solution exhibited a bright red color, while that of the Composition B solution exhibited an orange color. Bright red indicates that the solution contains significantly more amount of Sudan IV. The filtered dye-containing solution was stored at room temperature and periodically monitored for precipitation. No precipitation was observed in both solutions for 2 weeks. The results are listed in Table 12 below.

Table 12. Stability of Sudan IV-Containing Mixed Micelles

| Material composition | Material wt (gram) | Distilled Water (ml) | Solution Color | 14 day Stability |
|---|---|---|---|---|
| A | 0.18 | 6 | Bright red | No PPT |
|   | 0.19 | 6 | Bright red | No PPT |
|   | 0.19 | 6 | Bright red | No PPT |
| B | 0.19 | 6 | Orange | No PPT |
|   | 0.18 | 6 | Orange | No PPT |
|   | 0.18 | 6 | Orange | No PPT |

The above studies on Sudan IV-containing PLURONIC® Alloys demonstrates that the composition prepared according to the present invention exhibits (A) higher loading capacity for hydrophobic drugs, and (B) improved drug release profile than the best embodiments known to Applicant prepared as disclosed by the prior art. Moreover, the composition prepared according to the present invention is more compatible to the hydrophobic drug than the best embodiments known to Applicant prepared as disclosed by the prior art. The release of the hydrophobic drugs from the anhydrous, solid material of the present invention follows a distinct pattern that is substantially different and unanticipated. It is also obvious from the observation of the comparative dissolution patterns of the drug surrogate in this study that Sudan IV contained in the 60:40 blend of PLURONIC® P123 and F127 was released into the solution in the form of mixed micelles which exhibit higher drug loading capacity and micellar stability, while only a small amount of Sudan IV was incorporated into simple regular micelles in the dissolution of the prior art material.

Since Sudan IV is completely insoluble in water and cannot be dispersed in water in such a system, except through the dissolution of the dye in the core of the PLURONIC® micelles. This study thus shows the ability of the amphiphilic alloys prepared according to the present invention to store, or to preserve a highly hydrophobic drug in an anhydrous form for direct applications, or for subsequent dispersion and delivery in the form of a micellar drug or a mixed micellar drug.

For example, the filtered solution containing the micellar drug may be used directly for IV injection, or may be lyophilized and stored for future applications.

The lyophilized drug-containing PLURONIC® alloys can be used as is for direct applications onto skin, mucosa membranes, such as sublingual, or oral administration.

It may also be re-constituted by dispersion in sterile solution for injection application. The lyophilized drug-containing PLURONIC® alloys may also be blended, or melt blended with other suitable formulations including other amphiphilic block copolymer or block copolymer alloys for specific therapeutic needs. Furthermore lyophilized drug—containing PLURONIC® alloys prepared by methods other than the present invention, for example, by thin film dispersion, may also be melted and cooled to form microcrystallines according to the present invention in order to impart the desired beneficial properties.

Since the properties and characteristics of the amphiphilic block copolymer alloys prepared according to the present invention can be tailored by adjusting (A) the material formulation (such as the ratio of the high melting and low melting amphiphilic block copolymers, the molecular mass and the hydrophilic-lipophilic balance (HLB) of the individual amphiphilic block copolymer), and (B) the cooling rate of the molten block copolymers and thus the degree of crystallinity, drug-containing amphiphilic block copolymer alloys with physical consistencies ranging from grease, soft wax, and hard wax, and with varying surface properties, and critical micelle concentration (CMC) can be prepared and tailored for specific therapeutic applications, including health, beauty, medical, pharmaceutical and/or other therapeutic medical applications involving the controlled release of the active chemicals and/or corresponding synergetic agents.

EXAMPLE 14

Simulation of PLURONIC® Material Cooling Profiles

Figure 6:
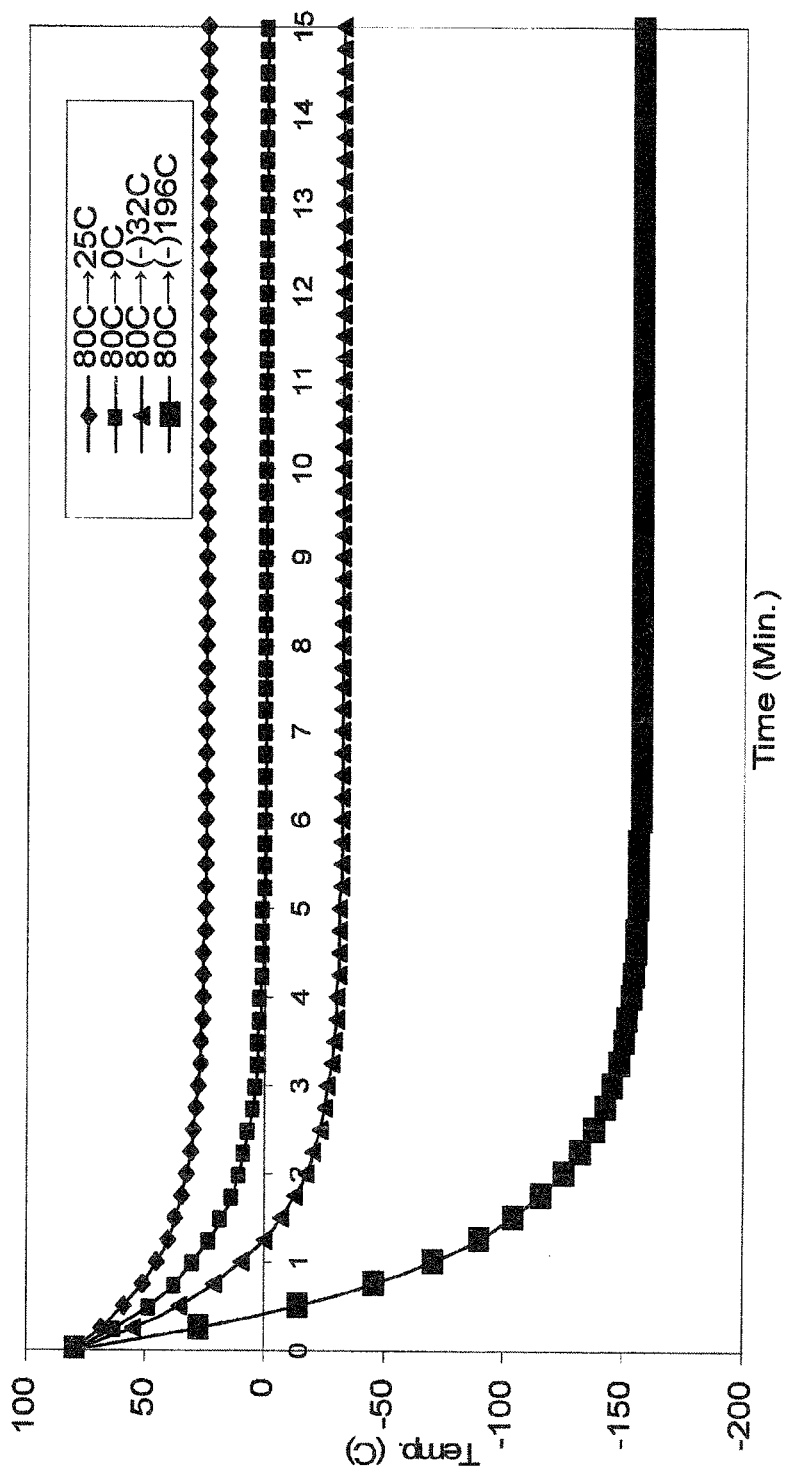
FIG. 6 shows the simulated cooling profiles of PLURONIC® alloy demonstrating the effect of mold temperature on cooling rate.

The cooling rate of a material, in general, is an exponential decay function, and can be represented by the following equation: $T \approx T2+(T1-T2)*EXP(-Kt)$; where T1 is the molten temperature of the material, T2 is the temperature of the cooling environment (or mold in this case), T is the temperature of the material at a given time, t, and K is a constant, which is related to the mass of the mold, the mass of the molten material, and the mold design such as surface contact area between the molten material and the mold. The cooling of a non-crystallizable material from 80° C. to an ambient (25° C.) and sub-ambient temperature (0° C., −32° C., and −196° C.) mold is simulated digitally and plotted in FIG. 6. The simulated cooling profiles for the 0° C. and −32° C. molds resemble the cooling profiles of the molten PLURONIC® blends cooled under the same conditions. There is no exothermic transition during the simulated cooling of the non-crystallizable material in a 0° C. and −32° C. mold. The initial first minute cooling rates of these simulated cooling profiles were calculated and found to be −35° C./min, −51° C./min, −71° C./min and −150° C./min, respectively for the simulated cooling at 25° C., 0° C., −32° C., and −196° C. molds. The cooling of the material at −196° C. (liquid nitrogen temperature) occurs at much faster rate than the rest of the cooling profiles.

The results of the simulation study indicate that (A) the cooling profiles of the blended PLURONIC® block copolymers follow an exponential decay function, (B) the cooling rate of the material is reversely proportional to the temperature of the mold, i.e., faster in a lower temperature mold, and (C) there is an exothermic event (absent in the simulation study) that takes place during the cooling of the PLURONIC® blend in a 25° C. mold.

Figure 7:
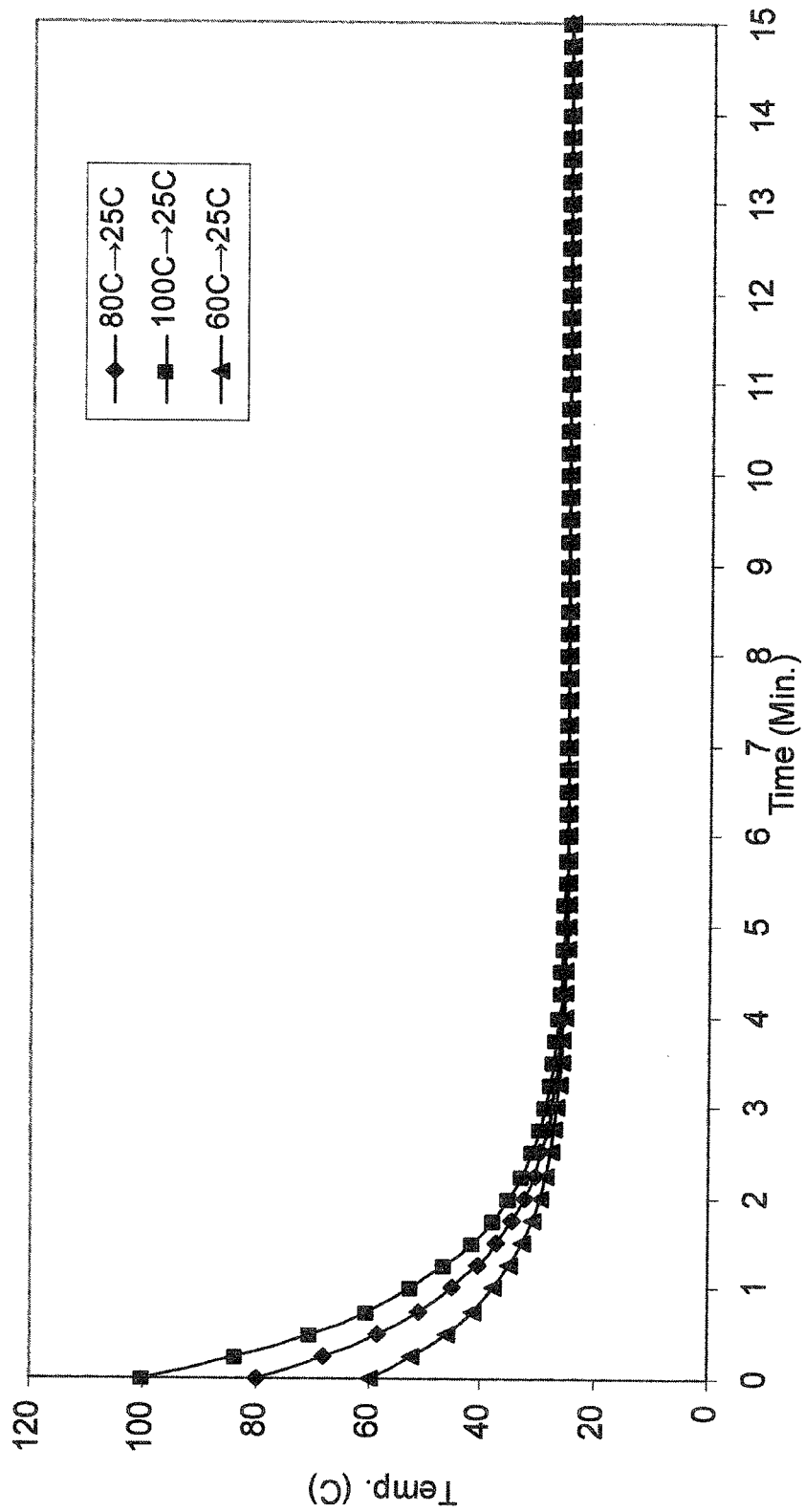
FIG. 7 shows the simulated cooling profiles of PLURONIC® alloy demonstrating the effect of molten temperature on cooling rate.

Separately, the effect of the molten temperature of a non-crystallizable material to the material's cooling rate in a mold temperature at 25° C. is also simulated and plotted in FIG. 7. This simulation shows that the material cooling rate is also affected by the molten temperature of the material. At a given temperature, the cooling rate is faster with the higher material molten temperature.

Since the exotherm of a phase transition, such as crystallization, is typically a function of time and temperature and can be represented by a Gaussian function, such as:

$$T=A*EXP(-(t-B)^2/2C^2)$$

Figure 8:
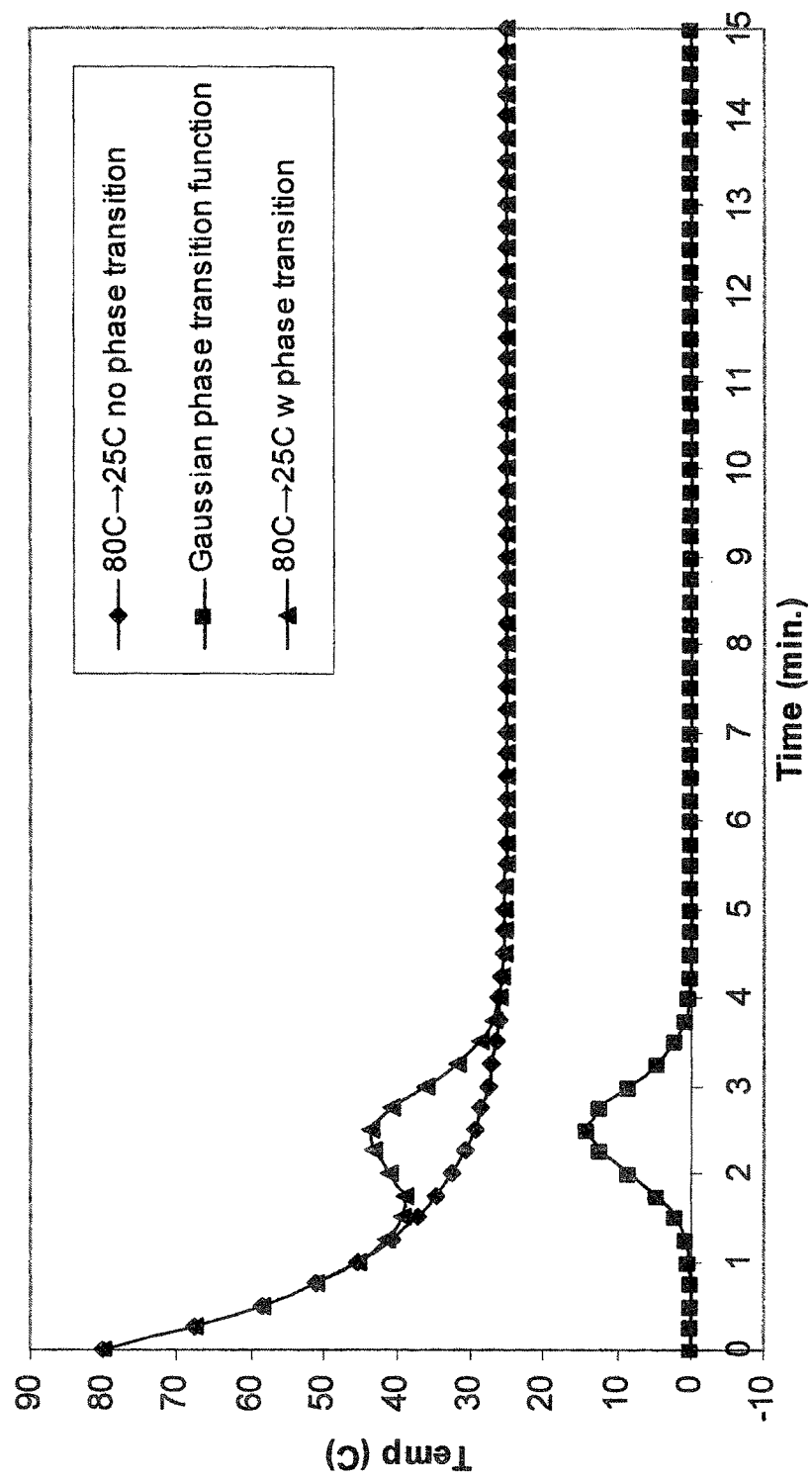
FIG. 8 shows the simulated cooling profiles of PLURONIC® alloy demonstrating the effect of phase transition on cooling profile.

Where, T is the elevation of the material temperature at a given time t, A is the peak height of the elevated temperature, B is the center location (time) of the Gaussian curve, and C is the width of the Gaussian curve. The cooling profile of a crystallizable material that induces phase transition, such as an exothermic crystallization, can be simulated by summing the corresponding exponential decay function and Gaussian function. FIG. 8 provides a simulated cooling profile of a 80° C. molten material that is crystallizable in a 25° C. mold, during which an exothermic phase transition takes place. The simulated cooling profile is constructed by summing the corresponding Gaussian function simulating the exotherm of a phase transition, and the corresponding simulated cooling profile of a non-crystallizable material without phase transition. The resulting cooling profile is similar to the cooling profiles of PLURONIC® F88 and F127 materials that show an exotherm. The degree of crystallinity is proportional to the amount of exotherm which can be determined by the size of the area enveloped between the cooling profile with an exotherm and the one without an exotherm.

Overall, these simulation studies further confirms that the non-exponential decay cooling profiles observed with the cooling of polymer alloy in a room temperature mold is caused by the exothermic phase transition of polymer crystallization, and demonstrates that the cooling rate of the molten blended copolymers can be adjusted, simulated and controlled, among others, by adjusting the temperatures of the molten material and the mold, respectively. Since crystallization is a kinetic process and only occurs below the melting point of the material and within a certain limited temperature range within which the polymer molecules can align and pack into crystalline structures. The amount and the characteristics, such as size and shape, of the microcrystallines, including lamella and spherulites, formed during the cooling of the block copolymer alloy is dependent upon the cooling rate, the amount of crystallizable component and the parameters of the molding process. These in turn can be controlled by adjusting the molten temperature of the material before the material is dispensed or injected into the mold, the mold temperature, the material formulation ratio, and the design of the molding system, including the mass of the mold, the cooling profile of the mold, and/or the pressure exerted on the molten material.

The material cooling profile in a forming or molding operation may be experimentally determined, simulated, refined and controlled numerically by computer (CNC) as described herein. The formation and the amount of microcrystalline generated in the molded amphiphilic block copolymer alloys can be determined or estimated by density measurement, differential scanning calorimetry (DSC), x-ray diffraction analysis and other analytical techniques, such as infrared spectroscopy or NMR. The formation and the amount of microcrystalline formed can also be estimated by comparative testing of a series of molded articles with different degree of crystallinity using a variety of other physical properties measurement instruments or methods. Temperature probes and/or temperature control feedback loop may be built into the molding machines to precisely control the material cooling profile, or specifically control a certain portion of the material cooling profile to produce amphiphilic block copolymer alloy materials with tailored amount of crystallinity and specific properties.

While the cooling process to induce microcrystalline formation is often conducted under static condition, it is known that other physical and chemical processes may also stimulate or interrupt the formation of crystalline during cooling. For example, applying high pressure may cause the polymer chains to fold into a more orderly and compact crystalline structure while agitation by blending, stirring, or flowing may impede the formation of large crystalline domains. In addition, if a polymer melt is forced through, e.g., a nozzle, such as a nozzle that is used in making fibers and films; it creates tensile stress to partially align its molecules. Such alignment can stimulate the formation of crystallization along its axis and affect the material properties.

While the above studies demonstrate that the cooling profile of a crystallizable polymer melt in a static cooling environment can be simulated and controlled by predetermined parameters, the cooling and microcrystalline moiety forming process of polymers in a dynamic condition can similarly be simulated, tuned and controlled using the same methodology if the dynamic conditions, such as, designed, parameters and functions are given. In the industry, the dynamic processes used can include blending, melting, injection molding, compression molding, extrusion, film forming and fiber forming processes. These processes are typically performed by automatic computer controlled machines, such as, mixing and blending machine, injection molding machines, compression molding machines, extrusion machines, film forming machines, and/or fiber forming machines, etc. The characteristics and specialty of each of the aforementioned process machinery and control are well documented in the respective fields.

Thus, one can utilize the method of the present invention to fine tune and control the formation, the quantity and the characteristics of polymer crystalline moieties, and the property of final material by choosing appropriate static or dynamic cooling conditions.

EXAMPLE 15

Bone Graft Carrier

The bone graft particle-containing compositions were prepared by mixing the bone graft particles with a molten 60:40 blend of PLURONIC® P123 and F127 alloy, or with a 0.5 wt % Sudan IV-containing 60:40 blend of PLURONIC® P123 and F127 alloy at 80° C. under vacuum for a period of 10 hours. The bone graft particle-containing mixture was dispensed into a 3 mm×11 mm×50 mm rectangular mold and allowed to cool to room temperature for 15 minutes. 30 minutes later, the molded parts were removed, placed in a sealed foil pouch and sterilized by gamma sterilization. The malleability of the sterilized material was tested and the results are listed in the Table 13 below.

TABLE 13

Properties of Bone Graft—Containing PLURONIC ® Alloys

| Binder Composition | 60:40 blend of P123 and F127 | | 0.5% Sudan IV in 60:40 blend of P123 and F127 | |
| --- | --- | --- | --- | --- |
| Bone Particle | Unigraft ® | Dembone | Unigraft ® | Dembone |
| Particle size | 200-400 um | 250-500 mu | 200-400 um | 250-500 mu |
| % Bone particles | 50 | 50 | 50 | 50 |
| Property | malleable | malleable | malleable | malleable |

Unigraft®: bioactive glass made by Unicare Biomedical, Inc.
Dembone: demineralized freeze dried bone powder made by Pacific Coast Tissue Bank.

An approximately 3 mm×6 mm disk (0.11 gram) was pouched out from each of the molded materials. The dissolution of the disks was studied as described earlier. It was found that as the PLURONIC® alloy gradually dissolved into the solution, the PLURONIC® bone graft matrix gradually disintegrated over a period of about 120 minutes, releasing the bone graft particles. In the case of Sudan IV-containing PLU- RONIC® bone graft matrix, the release of Sudan IV was found independent of the bone graft particles, and vice versa.

The release of Sudan IV takes place in the form of mixed micelles similar to that seen in Example 12, and both the Sudan IV and Unigraft® bioactive glass particles can be released upon dissolution simultaneously. These studies demonstrate that compositions prepared according to the present invention can be used as bone particle binder or matrix, and that both bone graft particles and drug can be co-incorporated in the PLURONIC® alloy composition for medical applications.

While this invention has been described with respect to various specific examples and embodiments, it is to be understood that the invention is not limited thereto and that it can be variously practiced within the scope of the following claims.

I claim:

1. A composition comprising a malleable, biocompatible substantially macroscopically homogeneous polymer comprising a plurality of microcrystalline components dispersed within an amorphous component, wherein said composition comprises a first polymeric component comprising a PEO-PPO-PEO triblock polymer, and a second polymeric component comprising a PEO-PPO-PEO triblock polymer, and said first and second polymeric components have different melting points, and wherein said composition does not contain a copolymer comprising a poly(alkylene)-poly(ethylene glycol) component.

2. The composition of claim 1 wherein the microcrystalline component is hydrophilic and the amorphous component is hydrophobic relative to the microcrystalline component.

3. The composition of claim 1 wherein the molecular mass of each of the first and second polymeric components is different, and is independently from about 5 kg/mole to about 25 kg/mole.

4. The composition of claim 3 wherein the molecular mass of each of the first and second polymeric components is independently from about 3 kg/mole to 9 kg/mole.

5. The composition of claim 1, which lacks a random copolymer.

6. The composition of claim 3, which lacks a random copolymer.

7. The composition of claim 1, which is substantially anhydrous.

8. The composition of claim 1, which is water soluble.

9. The composition of claim 3, which is water soluble.

10. The composition of claim 5, which is water soluble.

11. The composition of claim 1, which is structured to adhere to a biological structure selected from the group consisting of bone, skin and other body tissue.

12. The composition of claim 3, which is structured to adhere to a biological structure selected from the group consisting of bone, skin and other body tissue.

13. The composition of claim 5, which is structured to adhere to a biological structure selected from the group consisting of bone, skin and other body tissue.

14. The composition of claim 9, which is structured to adhere to a biological structure selected from the group consisting of bone, skin and other body tissue.

15. The composition of claim 3 having a form selected from the group consisting of grease, a film, implant, coating, bone wax, binder, drug carrier, tablet and capsule.

16. The composition of claim 3 in which the first and second polymer components have different average molecular weights.

17. The composition of claim 5 in which the first and second polymer components have different average molecular weights.

18. The composition of claim 6, in which the first and second polymer components have different average molecular weights.

19. The composition of claim 16 in which one of said first and second polymer component has a melting point less than 37° C. and the other polymer component has a melting point greater than 37° C.

20. The composition of claim 5 in which one of said first and second polymer component has a melting point less than 37° C. and the other polymer component has a melting point greater than 37° C.

21. The composition of claim 1 wherein the degree of crystallinity ranges from 1% to 25% as detected by a method selected from the group consisting of a) thermal cooling profile of the melt polymer; b) density measurement; c) differential scanning calorimetry (DSC); d) X-ray diffraction (XRD); e) infrared spectroscopy; (f) nuclear magnetic resonance (NMR); (g) polarized light microscopy, h) transmission electron microscopy, and physical or mechanical property testing.

22. The composition of claim 5 wherein the degree of crystallinity ranges from 1% to 25% as detected by a method selected from the group consisting of a) thermal cooling profile of the melt polymer; b) density measurement; c) differential scanning calorimetry (DSC); d) X-ray diffraction (XRD); e) infrared spectroscopy; (f) nuclear magnetic resonance (NMR); (g) polarized light microscopy, h) transmission electron microscopy, and physical or mechanical property testing.

23. The composition of claim 1 wherein the degree of crystallinity ranges from 25% to 50%.

24. The composition of claim 1 wherein the degree of crystallinity ranges from 50% to 80%.

25. The composition of claim 1 wherein the degree of crystallinity ranges from 40% to 65%.

26. A product useful for medicine or surgery, which comprises (a) a device selected from the group consisting of anchors, catheters, implants, plates, prostheses, screws, sutures, drug delivery device, and surgical instruments and (b) a composition comprised of a malleable, biocompatible substantially macroscopically homogeneous polymer comprising a plurality of microcrystalline components dispersed within an amorphous component, wherein said composition is made by a process comprising the steps:
   mixing together a first non-random amphiphilic block copolymer comprising a poly(ethylene oxide)-poly(propylene oxide)-poly(ethylene oxide) triblock and a second non-random amphiphilic block copolymer comprising a poly(ethylene oxide)-poly(propylene oxide)-poly(ethylene oxide) triblock while both co-polymers are molten to form a blended polymer alloy, and
   cooling the molten blended polymer alloy at a cooling rate sufficiently slow to permit the detection of an exotherm when the temperature of the molten alloy is monitored during cooling;
wherein said composition does not contain a copolymer comprising a poly(alkylene)-poly(ethylene glycol) component.

27. The product of claim 26, wherein said device is coated with the composition.

28. The product of claim 26, wherein said implant device is selected from the group consisting of a porous implant, a solid implant, a joint implant, a dental implant, an orthopedic implant, a cranial implant, and a skeletal implant.

29. The product of claim 26, wherein said device is made from ceramic, glass, hydroxyapatite, polyethylene, stainless steel, titanium, a polymer, or any combination thereof.

30. The product of claim 26, wherein said composition further comprises a bioactive agent.

31. The product of claim 30, wherein said bioactive agent is selected from the group consisting of antibodies, antigens, bone growth factors, chemokines, cytokines, demineralized bone matrix, enzymes, hormones, morphogenic proteins, nucleic acids, receptors, ligands, biological response modifier, and signaling molecules.

32. The product of claim 26, wherein said composition further comprises a therapeutic drug.

33. The product of claim 32, wherein said composition is further comprised of at least one therapeutic drug selected from the group consisting of an analgesic, an anesthetic, an antigen, an antibiotic, an anti-infective drug, a steroidal anti-inflammatory drug, a non-steroidal anti-inflammatory drug, an imaging and contrasting agent, a bone growth factor, a morphogenic protein, a photosensitizing agent, a radio therapeutic, and a chemotherapeutics drug.

34. A composition comprising a malleable, biocompatible substantially macroscopically homogeneous polymer comprising a plurality of microcrystalline components dispersed within an amorphous component, wherein said composition is made by a process comprising the steps:

mixing together a first non-random amphiphilic block copolymer comprising a poly(ethylene oxide)-poly(propylene oxide)-poly(ethylene oxide) triblock and a second non-random amphiphilic block copolymer comprising a poly(ethylene oxide)-poly(propylene oxide)-poly(ethylene oxide) triblock while both co-polymers are molten to form a blended polymer alloy, and cooling the molten blended polymer alloy at a cooling rate sufficiently slow to permit the detection of an exotherm when the temperature of the molten alloy is monitored during cooling;

wherein said composition does not contain a copolymer comprising a poly(alkylene)-poly(ethylene glycol) component.

35. The composition of claim 34, wherein the rate of cooling in said cooling step is slower than −25° C./min.

* * * * *